US011517612B2

(12) United States Patent
Sveinsson

(10) Patent No.: US 11,517,612 B2
(45) Date of Patent: *Dec. 6, 2022

(54) METHODS OF TREATING INFLAMMATORY SKIN DISORDERS

(71) Applicant: NEPSONE EHF, Reykjavik (IS)

(72) Inventor: Birkir Sveinsson, Bessastadahreppur (IS)

(73) Assignee: NEPSONE EHF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 16/888,709

(22) Filed: May 30, 2020

(65) Prior Publication Data
US 2020/0338169 A1    Oct. 29, 2020

Related U.S. Application Data

(63) Continuation of application No. 15/355,723, filed on Nov. 18, 2016, now Pat. No. 10,668,132.

(51) Int. Cl.
| *A61K 38/22* | (2006.01) |
| *A61P 17/06* | (2006.01) |
| *A61K 9/00* | (2006.01) |
| *A61P 17/02* | (2006.01) |
| *A61K 38/23* | (2006.01) |

(52) U.S. Cl.
CPC .......... *A61K 38/225* (2013.01); *A61K 9/0014* (2013.01); *A61K 38/23* (2013.01); *A61P 17/02* (2018.01); *A61P 17/06* (2018.01)

(58) Field of Classification Search
None
See application file for complete search history.

(56) References Cited

U.S. PATENT DOCUMENTS

| 5,851,556 | A  | 12/1998 | Breton et al. |
| 5,932,215 | A  | 8/1999  | De Lacharriere et al. |
| 5,935,586 | A  | 8/1999  | De Lacharriere et al. |
| 6,019,967 | A  | 2/2000  | Breton et al. |
| 6,214,816 | B1 | 4/2001  | Hohlweg et al. |
| 6,313,097 | B1 | 11/2001 | Eberlein et al. |
| 8,168,592 | B2 | 5/2012  | Gegg, Jr. et al. |
| 9,585,940 | B2 | 3/2017  | Sveinsson et al. |
| 10,668,132 | B2 | 6/2020 | Sveinsson |
| 2003/0185824 | A1 | 10/2003 | Vaishnaw et al. |
| 2011/0150890 | A1 | 6/2011 | Sveinsson et al. |

FOREIGN PATENT DOCUMENTS

| WO | WO-9809630 A1 | 3/1998 |
| WO | WO-9856779 A1 | 12/1998 |
| WO | WO-0018764 A1 | 4/2000 |
| WO | WO-0055154 A1 | 9/2000 |
| WO | WO-2004014351 A2 | 2/2004 |
| WO | WO-2009033809 A2 | 3/2009 |
| WO | WO-2018022664 A1 | 2/2018 |

OTHER PUBLICATIONS

Evstaf'ev (vestnik Dermatologii I Venerologii; Jan. 1989 (9); 71-71 Abstract).*
Abstracts, 1992 annual meeting European Society for Dermatological Research, London, England, J Invest Dermatol 98:503-546 (1992).
Anand et al. Neuropeptides in skin disease: increased VIP in eczema and psoriasis but not axillary hyperhidrosis. Br J Dermatol. 124:547-549 (1991).
Bjarnason et al. Objective non-invasive assess-ment of patch tests with the laser doppler perfusion scanning technique. Contact Dermatitis. 40:251-260 (1999).
Bowen et al. Tumor necrosis factor-alpha stimulation of calcitonin gene-related peptide expression and secretion from rat trigeminal ganglion neurons. J Neurochem. 96:65-77 (2006).
Brain et al. Substance P regulates the vasodilator activity of CGRP. Nature 335(6185):73-5 (1988).
Braun-Falco et al. Structural aspects of initial psoriatic lesions. Arch. Dermatol. Forsch. 251(2):95-110(1974).
Burgess et al. Possible dissociation of the heparin-binding and mitogenic activities of heparin-binding (acidic fibroblast) growth factor-1 from its receptor-binding activities by site-directed mutagenesis of a single lysine residue. J Cell Biol. 111:2129-2138 (1990).
Christophers. The immunopathology of psoriasis. Int Arch Allergy Immunol. 110:199-206 (1996).
Claudy. Les Neuromediateurs En Dermatologie. Perspectives Therapeutiques. Path Biol 44(10):888-894 (1996).
Co-pending U.S. Appl. No. 16/888,708, filed May 30, 2020.
Co-pending U.S. Appl. No. 16/888,711, filed May 30, 2020.
Cuesta et al. Substance p and calcitonin gene-related peptide increase IL-1 beta, IL-6 and TNF alpha secretion from human peripheral blood mononuclear cells. Neurochem Int. 40:301-306 (2002).
Dewing. Remission of psoriasis associated with cutaneous nerve section. Arch Dermatol 104:220-221 (1971).
Dong et al. Calcitonin gene-related peptide regulates the growth of epidermal stem cells in vitro. Peptides 31:1860-1865 (2010).

(Continued)

*Primary Examiner* — Julie Ha
*Assistant Examiner* — Tara L Martinez
(74) *Attorney, Agent, or Firm* — Wilson Sonsini Goodrich & Rosati

(57) ABSTRACT

A method for treating, remedying, or preventing inflammatory skin disorders by administering a therapeutically effective dose of at least one an antagonist of a calcitonin gene-related peptide receptor in a pharmaceutically acceptable formulation. The method for treating, remedying, or preventing an inflammatory skin disorder by administering topically and to the pre-psoriatic rim a therapeutically effective dose of at least one an antagonist of a calcitonin gene-related peptide receptor in a pharmaceutically acceptable formulation.

2 Claims, 17 Drawing Sheets

(17 of 17 Drawing Sheet(s) Filed in Color)

Specification includes a Sequence Listing.

(56) References Cited

OTHER PUBLICATIONS

Farber et al. Is psoriasis a neuroimmunologic disease? Int. J. Dermatol. 38:12-15 (1999).
Farber et al. Stress, symmetry, and psoriasis: possible role of neuropeptides. J Am Acad Dermatol. 14:305-311 (1986).
Farber et al. The role of cutaneous sensory nerves in the maintenance of psoriasis. Int J Dermatol. 29:418-420 (1990).
Foster et al., Calcitonin gene-related peptide is chemotactic for human t lymphocytes. Ann N Y Acad Sci 657:397-404 (1992).
Gillardon et al. Ultraviolet irradiation of the skin attenuates calcitonin gene-related peptide mRNA expression in rat dorsal root ganglion cells. Neurosci. Lett. 124(2):144-7 (1991).
Goodfield et al. Investigations of the 'active' edge of plaque psoriasis: vascular proliferation precedes changes in epidermal keratin. British J. Dermatol. 131:808-813 (1994).
He et al. Calcitonin Gene-Related Peptide in Langerhans Cells in Psoriatic Plaque Lesions. Chin Med. J. 113(8):747-751 (2000).
He et al. Calcitonin gene-related peptide induces chemokine interleukine-8 synthesis in human monocytes. Natl. Med Journal, Zhonghua Yi Xue Za Zhi 82:131-134 (2002).
He et al. Regulation of the neuropeptide calcitonin gene-related peptide in chemotactic function of monocytes in psoriasis. Journal of Clinical Dermatology 31(7):407-409 (2002) (English Abstract).
Hull et al. Active and inactive edges of psoriatic plaques: identification by tracing and investigation by laser—Doppler flowmetry and immunocytochemical techniques. J. Invest. Dermatol. 92(6):782-5 (1989).
Jiang et al. Double-labeled immunofluorescence study of cutaneous nerves in psoriasis. Int. J. Dermatol. 37:572-574 (1998).
Khalil et al. Sensory Peptides as Neuromodulators of Wound Healing in Aged Rats. J. Geronol. Biol. Sciences 51A:B354-B361 (1996).
Kierland. Psoriasis: Proceedings of the international symposium-Stanford University 1971. Archives of Dermatology 106:137 (1972).
Krueger et al. Inflammatory and immune cell function in psoriasis: II. monocyte function, lymphokine production. J Invest Dermatol. 71:195-201 (1978).
Lazar et al. Transforming growth factor alpha: mutation of aspartic acid 47 and leucine 48 results in different biological activities. Mol Cell Biol. 8:1247-1252 (1988).
Lida et al. Morphology of live retinal pigment epithelial cells. Nippon Ganka Gakkai Zasshi 95(5):421-7 (1991) (English Abstract).
McLeod. Observations of fenestrated capillaries in the human scalp. J. Invest. Dermatol. 55(5):354-7 (1970).
Naukkarinen et al. Immunohistochemical analysis of sensory nerves and neuropeptides, and their contacts with mast cells in developing and mature psoriatic lesions. Arch. Dermatol. Res. 285:341-346 (1993).
Naukkarinen et al. Quantification of cutaneous sensory nerves and their substance p content in psoriasis. J Invest Dermatol 92:126-129 (1989).
Naukkarinen et al. Quantitative analysis of contact sites between mast cells and sensory nerves in cutaneous psoriasis and lichen planus based on a histochemical double staining technique. Arch Dermatol Res. 283:433-437 (1991).
Naukkarinen et al. Quantitative histochemical analysis of mast cells and sensory nerves in psoriatic skin. J Path 180:200-205 (1996).
Nickoloff et al. Characterization of a t cell line bearing natural killer receptors and capable of creating psoriasis in a SCID mouse model system. J Dermatol Sci. 24:212-225 (2000).
Nickoloff et al. Recent insights into the immunopathogenesis of psoriasis provide new therapeutic opportunities. J Clin Invest. 113:1664-1675 (2004).
Onuoha et al. Levels of vasodilators (SP, CGRP) and vasoconstrictor (NPY) peptides in early human burns. EurJ Clin Invest. 31:253-257 (2001).
Orecchia et al. Alopecia areata: more on topical sensitizers. Dermatologica 180:57-59 (1990).

Park et al. Factors influencing psoriasis: an analysis based upon the extent of involvement and clinical type. J Dermatol. 25:97-102 (1998).
Paus et al. Neural Mechanisms of hair growth control J. Invest. Dermatol. Symp. Proc. 2(1):61-68 (1997).
PCT/IS03/00023 International Search Report dated Apr. 13, 2004.
Pincelli et al. Neuropeptides in skin from patients with atopic dermatitis: an immunohistochemical study. Br J Dermatol. 122:745-750 (1998).
Pincelli et al. Substance p is diminished and vasoactive intestinal peptide is augmented in psoriatic lesions and these peptides exert disparate effects on the proliferation of cultured human keratinocytes. J Invest Dermatol. 98:421-427 (1992).
Pincelli. Neuropeptides and Psoriasis. Psoriasis 3rd ed. 1998, ed.: Roenikg, H.H.; Maibach H.I., Marcel Dekker Inv. NY (pp. 393-397).
Pinkus et al. The primary histologic lesion of seborrheic dermatitis and psoriasis. J. Invest. Dermatol. 46(1):109-16 (1966).
Psoriasis. MedlinePlus Medical Encyclopedia, [online]. Update date: Nov. 22, 2011. U.S. National Library of Medicine, NIH. [retrieved on Sep. 21, 2012]. Retrieved from the Internet: <URL:http://www.nlm.nih.gov/medlineplus/ency/article/000434.htm> (pp. 1-5).
Ravchauduri et al. Neuropeptides and neurogenic Inflammation in Psoriasis. Psoriasis 3rd Ed., Roenikg and Maibach Marcel Dekker Inv. NY pp. 383-391 (1998).
Raychaudhri et al. Are sensory nerves essential for the development of psoriatic lesions? J Am. Acad. Dermatol. 28(3):488-489 (1993).
Raychaudhri et al. Psoriatic Keratinocytes Express High Levels of Nerve Growth Factor. Acta Derm Ven Mar. 78:84-86 (1998).
Rossi et al. Possible involvement of neuropeptidergic sensory nerves in alopecia areata. Neuroreport 8:1135-1138 (1997).
Sholley et al. Endothelial DNA synthesis in themicrovasculature of rat skin during the hair growth cycle. Am. J. Anat. 147(2):243-54 (1976).
Takahashi et al. Direct effects of cutaneous neuropeptides on adenylyl cyclase activity and proliferation in a keratinocyte cell line: stimulation of cyclic AMP formation by CGRP and VIP/PHM, and inhibition by NPY through G protein-coupled receptors. J Invest Dermatol. 101:646-651 (1993).
Talme et al. The neuropeptide calcitonin gene-related peptide (CGRP) stimulates T cell migration into collagen matrices. J Neuroimmunol. 196:60-66 (2008).
Tang et al. Changes of CGRP levels in plasma and CGRP mRNA in dorsal root ganglia during endotoxicosis in the rat. Sheng LiXue Bao 49(2):160-6 (1997) (English Abstract).
U.S. Appl. No. 10/524,104 Office Action dated Aug. 30, 2007.
U.S. Appl. No. 10/524,104 Office Action dated Jun. 23, 2008.
U.S. Appl. No. 10/524,104 Office Action dated Mar. 20, 2009.
U.S. Appl. No. 10/524,104 Office Action dated Sep. 2, 2010.
U.S. Appl. No. 13/039,075 Office Action dated Dec. 21, 2011.
U.S. Appl. No. 13/039,075 Office Action dated Jul. 20, 2012.
U.S. Appl. No. 13/969,288 Office Action dated Mar. 24, 2016.
U.S. Appl. No. 13/969,288 Office Action dated Nov. 17, 2016.
U.S. Appl. No. 15/355,723 Office Action dated Dec. 19, 2019.
U.S. Appl. No. 15/355,723 Office Action dated May 30, 2019.
Wallengren et al. Phototherapy reduces the number of epidermal and CGRP-positive dermal nerve fibres. Acta Derm Venereol 84(2):111-115 (2004).
Wallengren et al. Substance p and vasoactive intestinal peptide in bullous and inflammatory skin disease. Acta Derm Venereol. 66:23-28 (1986).
Wallengren. Substance P antagonist inhibits immediate and delayed type cutaneous hypersensitivity reactions Br. J. Dermatol. 124(4):324-8 (1991).
Wang et al. Production and secretion of calcitonin gene-related peptide from human lymphocytes. J Neuroimmunol. 130:155-162 (2002).
Weddell et al. Psoriatic Skin. Arch Dermatol. 91:252-266 (1965).

(56) References Cited

OTHER PUBLICATIONS

Weidner et al. Acute effects of substance p and calcitonin gene-related peptide in human skin—a microdialysis study. J Invest Dermatol. 115:1015-1020 (2000).

Wolf et al. Measurement of the skin-cleaning effects of soaps. Int. J. Dermatol. 3(8):598-9 (1993).

Wollina. The effect of neuropeptides on wound healing in vitro and in vivo. Hautarzt 43:616-620 (1992).

Wrone-Smith et al. Dermal injection of immunocytes induces psoriasis. J Clin Invest. 98:1878-1887 (1996).

Wu et al. Development and potential of non-peptide antagonists for calcitonin-gene-related peptide (CGRP) receptors: evidence for CGRP receptor heterogeneity. Biochem. Soc. Trans. Aug. 30(4):468-473 (2002).

Xing et al. Induction and expression of beta-calcitonin gene-related peptide in rat t lymphocytes and its significance. J Immunol. 165:4359-4366 (2000).

Yahya. Acne vulgaris in Nigerian adolescents—prevalence, severity, beliefs, perceptions, and practices. Int. J. Dermatol. 9:418-20 (1990).

Zochodne et al. Evidence for CGRP accumulation and activity in experimental neuromas. Am. J. Physiol. 268(2pt2):H584-90 (1995).

Braverman, in Psoriasis 3rd ed. (pp. 399-407), 1998, ed.

Camp. Chapter 31: Psoriasis. in Textbook of Dermatology. R.H. Champion, J.L. Burton & F.J.G. Ebling, Eds., Fifth Edition, Blackwell Scientific Publications (pp. 1391-1457) (1992).

Novotny. Psoriasis Treatment by Heparin. ACTA Universitatis Carolinae Medica 31(3/4):243-245 (1985).

U.S. Appl. No. 16/888,708 Office Action dated Feb. 2, 2021.
U.S. Appl. No. 16/888,708 Office Action dated Jul. 9, 2021.
U.S. Appl. No. 16/888,708 Office Action dated Oct. 16, 2020.
U.S. Appl. No. 16/888,711 Office Action dated Feb. 4, 2021.

Wilkinson et al. Chapter 16: Contact Dermatitis. in Textbook of Dermatology, R.H. Champion, J.L. Burton & F.J.G. Ebling, Eds., Fifth Edition, Blackwell Scientific Publications (pp. 611-715) (1992).

* cited by examiner

METHODS OF TREATING INFLAMMATORY SKIN DISORDERS

CROSS-REFERNCE

This application is a continuation of U.S. patent application Ser. No. 15/355,723, filed Nov. 18, 2016, now U.S. Pat. No. 10,668,132, which application is incorporated herein by reference in its entirety.

SEQUENCE LISTING

The instant application contains a Sequence Listing which has been submitted electronically in ASCII format and is hereby incorporated by reference in its entirety. Said ASCII copy, created on May 30, 2020, is named "54955710302_SL.txt" and is 1,048 bytes in size.

FIELD OF THE INVENTION

This invention relates to compositions and compounds that are CGRP antagonists, or reduces its activity for use in particular for treating and or preventing psoriasis.

Psoriasis is a chronic skin disorder that afflicts about 2 percent of the population. The disease is associated with the rapid turnover of skin cells (hyperproliferation) accompanied by a loss of differentiation so that silvery white scales form on the surface of the skin. Additionally, the capillaries become tortuous and dilated and an inflammatory reaction occurs, so that the skin reddens. The elevated silvery white scales on a contrasting red background produce the unsightly lesions characteristic of psoriasis. Psoriasis most commonly appears on the scalp, knees, elbows, hands and feet, but can affect any part of the skin. The cause of the disease is unknown, though it is believed to have a genetic component, and it has been suggested to be a T-cell mediated autoimmune skin disorder. There have been many attempts to treat the disease, and several topical and systemic treatments for psoriasis which inhibit cell division have been tried, with limited success in clearing the skin for short periods of time. Yet, the reason why these treatments work is not yet clearly understood. Treatments which have been suggested in the art appear to be symptomatic and palliative. Lesions may disappear spontaneously or as a result of the therapy, but recurrences are likely.

The present invention is directed to methods of treatment of psoriasis based on observations and new findings that strongly indicate that psoriasis is a disease of the nervous system, and that the neuropeptide calcitonin gene-related peptide (CGRP) is a major mediator of the disease.

CGRP is a 37 amino acid polypeptide that is stored and released from nerve terminals in both the central nervous system and the peripheral nervous system. CGRP has been detected in nerves innervating the heart, peripheral and cerebral blood vessels, and kidneys by immunohistochemical (such as ELISA) and radioimmunoassay methods. CGRP has been shown to mediate its biological response by binding to specific cell surface receptors that have been identified in a variety of tissues.

CGRP also is a very important neuropeptide (NP) in wound healing and is the first NP that is released during that process. CGRP is a very strong vasodilator and is a strong inhibitor of delayed type hypersensitivity (DTH). CGRP is known to play a role in the regulation of hair growth, and can stimulate the proliferation of keratinocytes.

Tryptase is a protease enzyme that cleaves CGRP and reduces its activity. CGRP 8-37 is an endogen peptide that is made from CGRP by specific cleavage by tryptase. CGRP 8-37 is a high affinity antagonist for the CGRP receptor. It is thought that this antagonist is an endogen compound used by the body for the down-regulating neural signals (negative feedback control).

More capillary loops are seen in papillary dermis in psoriasis than healthy skin. These vessels in the horizontal plexus are an integral component of the lesions in psoriasis vulgaris and pustular psoriasis of von Zumbusch. The capillary loops in the papillary dermis of psoriatic lesions become. dilated and tortuous before epidermal hyperplasia has been detected morphologically. Based upon light microscopic studies of developing psoriatic lesions, Pinkus and Mehthregan have concluded that initial vasodilatation accompanied by an exudation of inflammatory cells and serum in the papilla is the initiating event in psoriasis (Pinkus, Mehthregan J. Invest. Dermatol. 1966 January; 46(1):109-16).

Several investigators, who studied developing 1-mm psoriatic lesions, found an upward proliferation of the dermal papillae at edges of psoriatic lesions. They believed this enlargement was one of the initiating events, although the stimulus was unknown (see e.g. Braun Falco and Cristophers, Arch. Dermatol Forsch. 1974; 251(2):95-110). Braverman et al. found based upon the pattern by which the loops in psoriasis vulgaris return to normal and the pattern of vascular labeling in Zumbuch disease, the mechanism how the capillary loop develops. The endothelial cells in the extrapapillary venous limb enlarges and the arterial part becomes shorter as the papilla enlarges. The venous part becomes fenestrated (Braverman, I. M., in Psoriasis 3rd ed. (pp. 399-407), 1998, ed.: Roenikg, H. H.; Maibach H. I., Marcel Dekker Inc., NY).

An analogous phenomenon develops in the microvasculature of rat skin during the hair growth cycle (Sholley and Cotran Am. J. Anat. 1976 October; 147(2):243-54). The capillary network around actively growing follicle (anagen phase) increases in size by endothelial cell proliferation. Virtually all the endothelial cells are supplied by the capillaries. In human skin, both glabrous (Braverman, I. M. supra) and scalp (McLeod, W. A.; J. Invest. Dermatol., 1970, 55(5), 354-7), the capillary network around the hair follicles has a venous ultrastructure: bridge fenestration and a laminated basal membrane. When the rat hair follicle enters catagen, the vascular network is greatly reduced in size, partly through loss and partly through collapse.

The growth cycle of hair is a well-known phenomenon. Hair follicles grow in repeated cycles. One cycle can be broken down into three phases: anagen (growth phase), catagen (transitional phase), and telogen (resting phase). In any one time, about 85% of hairs of all hairs are in anagen phase. At the end of anagen phase the hairs enter into catagen phase, which lasts about one or two weeks. The telogen phase follows the catagen phase and normally lasts about 5-6 weeks. Approximately 10-15% of all hairs are in this phase at any one time. The reason why such a relatively large fraction of hairs are in telogen phase can be that they are thus prepared to act in keratinocyte proliferation in case of wound healing. To do so, a common factor will have to act in the regulation of early wound healing and regulation of the hair growth cycle. CGRP provides this role.

It is here postulated that CGRP turns hair follicles to proliferative phase to bring stem cell keratinocytes to the surface to participate in keratinocyte proliferation of the epidermis when the skin is healing. The keratinocytes come from the outer root sheath or the papilla dermis of the hair follicle. This is further supported by the fact that neuropeptides are thought to play a major role in regulating hair growth (see, e.g., J. Invest. Dermatol. Symp. Proc. 1997; 2(1), 61-68).

Studies have shown that the dermal papilla is probably the primary target in alopecia areata (AA). This is why CGRP is a common actor on these stem cells both in AA and psoriasis. Psoriatic keratinocytes which are all of a specific subtype are thought to come from the stem cells located in the hair follicle.

As described in the accompanying Example 4, it has been observed that psoriasis frequently appears with a hexagonal structure in the skin, that is, the psoriasis lesions appear as hexagons, both as singly isolated and also interconnected in a honeycomb pattern. It is postulated herein that these hexagons may represent neurological units of sensory innervation. This may indicate that one or more neural segments or units are involved when psoriasis lesions develop. There is a similarity in distribution and shape of Herpes Zoster (Viral nerve infection) lesions (see Example 5). This further supports the theory that the pattern of psoriasis is indicative to neural origin of the disease.

Six-corner (hexagonal) shape lesions in psoriasis are for the most part of fixed size for a given part of the body, as shown in Example 4. The exact structure of the nerve innervations in the skin has never been described in detail but the hexagonal shape is widely seen in nature as in the bee cube and in the portal system of the liver.

The most common localizations of psoriasis lesions can be explained based on neural origin of psoriasis. Striking symmetry of the lesions is common and lesions are located in areas that are known or likely nerve overlap areas, as e.g. the navel, lower back, temporal scalp region, elbows and knees. On the scalp and on the sacral area are very likely embryonic parts of the neural crest that are the last to close in the fetal development of the skin. This is further supported by the fact that aplasia cutis absence of skin most often is located on the scalp in the right temporal area, and spina bifida is located in the lumbosacral area. Location of psoriasis in the scalp, lumbosacral area, elbows and knees are particularly interesting. If one thinks of an animal on four legs, these parts are the rear, the front, and the prominent part of the extremities. Psoriasis lesions often appear at the same spots on the skin repeatedly, i.e. with a memory effect. This is the same as often seen in herpes simplex infections (viral nerve infection in peripheral skin). I have seen clinical case of a psoriasis patient that had psoriasis lesions distributed along a dermatome (nerve innervation area). The same pattern is seen in Herpes Zoster infection (viral nerve infection).

It has been observed by the Inventor that psoriasis lesions can be distributed over nerve innervation area on the hands.

Individual keratinocytes in the skin also have hexagonal form. Psoriatic keratinocytes express high levels of NGF (nerve growth factor) which stimulates growth of nerves in the skin. (Acta Derm Ven March 1998.84-86) Reports of psoriasis getting better after sensory nerve damage is further clinical evidence supporting the role of nerves in the pathogenesis of psoriasis. (J. of the Am. Acad. Dermatol. 28, 3, 488-489; Int. J. Dermatol. 1990; 9:418-20).

Several other observations support the thesis underlying the current Invention, that psoriasis is a neurogenerative disease, though this has not been clearly indicated in the prior art. Psoriasis developed contra lateral to hemi paresis following cerebrovascular accident. (Int. J: Dermatol. 3 (8): 598-9 1993 August). Patients with leprosy have destruction of peripheral nerves. It has also been noted that leprosy patients have decreased incidence of psoriasis. CGRP increases with neural trauma. CGRP 8-37 (a CGRP antagonist, described below) blocks its increase (Am. J. Physiol. 268 (2pt2) H584-90 1995 February). Prompt remission of a psoriatic plaque has been reported following cutaneous nerve sectioning. (Dewing, S. B. Arch Dermatol 104:220-221 1971).

In an investigation by means of fluorescein angiography, the retinal pigment epithelial cells in pigmented rabbits were observed. A hexagonal pattern was regularly seen away from the medullar rays. The pattern became larger at the periphery than in the posterior pole. These angiographic findings closely matched those of retinal pigment epithelial cells as seen by scanning electron microscopy and fluorescein light microscopy in sizes and shapes. This pattern in the sensory innervation in the retina is similar to that described herein for neural units of the skin. The hexagonal pattern in the skin becomes larger in the periphery, i.e. on the extremities. (Lida et al. Nippon-Ganka Gakkai Zasshi 1991, 95(5):421-7)

CGRP and Substance P (SP) in psoriasis and possible coordination in nerve function.

Farber et al. first proposed in 1986 a possible role for neuropeptides in the pathogenesis of psoriasis (see review in Raychaudhuri, P., Farber, E. M. in Psoriasis 3rd ed. (pp. 383-391), 1998, ed.: Roenikg, H. H.; Maibach H. I., Marcel Dekker Inc., NY. Researchers have focused in particular on SP, and some SP antagonists have been suggested for treating psoriasis, e.g. Somatostatin and Spantide (Farber et al., supra). Both SP and CGRP are often located in the same nerves in the skin. SP and CGRP are both active in wound healing, CGRP in the early phase and SP later. Reports show high density of SP and CGRP in psoriasis skin, see e.g. Jiang et al. Int. J. Dermatol. 1998, 37, 572-574.

The substance P antagonist Spantide inhibits immediate and delayed type cutaneous hypersensitivity (DTH) reaction. This could be mediated through CGRP as it is known that CGRP suppresses DTH, thus SP might act as a regulator for CGRP. (Wallengren J. Br. J. Dermatol., 1991, 124(4): 324-8)

Substance P regulates the vasodilator activity of CGRP. Experiments in animals revealed that this phenomenon is dependent on proteases from mast cells. (Brain S. D.; Williams, T. J. "Substance P regulates the vasodilator activity of CORP" Nature 1988 335(6185), 73-5). These experiments showed that SP converts the long lasting vasodilatation induced by CGRP into a transient response when these neuropeptides were injected into human skin. A subsequent study (J. Geronol.: Biol. Sciences 1996; Vol. 51A, No, B354-B361) used a "blister model in the rat hind footpad" to demonstrate the ability of SP to terminate an existing vasodilator response to CGRP. The results are seen as not only confirming that combined administration of SP and CGRP in human skin can limit the vasodilator activity of CGRP, but also that a modulator inhibitory effect exerted by SP on the vasodilator activity is dose-dependent. This statement could indicate that SP changes in psoriasis are mainly of regulatory (secondary) nature.

Reports by Haukkarinen et al. (Haukkarinen et al. Journal of Pathology, (1996) 180, 200-205) describe studies of contact values between sensory nerves containing SP, CGRP, and VIP, and mast cells containing active tryptase and inactive chymase. The contact values of SP and CGRP with mast cells are increased in psoriatic lesions, whereas contact values for VIP are decreased. Tryptase effectively cleaves CGRP as well as VIP but not SP, whereas chymase cleaves SP. This points to a controlling mechanism in psoriasis acting to increasing cleavage of CGRP but not SP, i.e. active tryptase is increased in order to try to down-regulate CGRP, but active chymase is not increased.

In psoriasis, reduced tryptase activity may be the key step in increasing CGRP activity. This is possibly because a specific step in down-regulation (negative feedback) of CGRP is missing, because CGRP 8-37 is not being produced sufficiently. This modified peptide is a high-affinity antagonist to the CGRP receptor, as discussed above. If a specific tryptase in psoriasis is not correctly built and dysfunctional, it can have substantial influence on CPGRP activity. Several mutations in genes coding for tryptase can be responsible for this. Differing severity of psoriasis can be explained by different mutations in the specific tryptase. Thus, if this is the case, psoriasis can be explained by an alteration in one enzyme system, and possibly just by alteration in a single amino acid for any given subtype of psoriasis, in the enzyme tryptase. Certain observations support this notion, for example, smoking is known to increase likelihood of psoriasis, and smoking is also known to cause defects in tryptase in lungs. This would, however, not change the effect of the present invention, that by blocking CGRP, psoriasis may be treated or prevented. This hypothesis could be readily verified by screening tryptase (or the gene coding for tryptase) from psoriasis patients and control groups to identify possible gene defects.

Several other factors point to CGRP being a much more likely mediator in psoriasis than SP. CGRP does not induce itch but SP does, and itch is most often not a symptom associated with psoriasis; CGRP does not produce weal and flare as much as SP, and SP is very active in conducting pain and burning sensation, neither of which are normally symptoms of psoriasis. CGRP however produces prolonged erythema, which is associated with psoriasis, but SP does not.

Guttae psoriasis is often seen following streptococcal infection. Several groups of streptococci can induce this. These bacteria have in common that they all produce exotoxin C, a pyrotoxin that induces vasodilatation when injected into the skin. This was used in the past as a diagnostic test of streptococcal infection known as the Dicks test. Experimental work from Beijing Medical University has shown that rats that are given endotoxin have increased level of CGRP in plasma (Tang et al. Sheng Li Xue Bao 1997 April; 49(2):160-6 (Medline abstract PMID: 9812851)). CGRP is released from sensory neurons and also is the transcription of CGRP mRNA and synthesis of CGRP, in sensory neurons increased during the development of endotoxicosis in the rat. Repeated injections of endotoxin from *Staphylococcus* induced hyperkeratosis. in immunodeficiency mice. The onset of psoriasis in the wake of streptococcal infection can thus be-explained by an increase in CGRP.

All the aforementioned facts and described observations strongly indicate that CGRP is a key mediator in psoriasis, which has subsequently inspired the current invention that relates to methods of treatment for psoriasis based on the use of specific CGRP antagonists.

Several compounds have been found to selectively inhibit the CGRP receptor, such as small molecular non-peptide compounds, peptides and antibodies. Such active CGRP antagonists are expected to be useful in the treatment of a variety of disease states that are mediated-by CGRP. Diseases that such treatment has been suggested for include headaches, esp. migraines; NIDDM; neurogenic inflammation; cardiovascular disorders; chronic inflammation; pain; endotoxic shock; arthritis; allergic rhinitis; allergic contact dermatitis; inflammatory skin conditions; and asthma. Such compounds however, have not to my knowledge been suggested for treatment of psoriasis.

Compounds disclosed in the prior art found to be useful as antagonists of CGRP include 4-sulfinyl benzamide compounds (WO 98/56779), 3,4-dinitrobenzamide compounds (WO 98/09630), a group of modified amino acids (WO 00/55154), and benzamidazolinyl piperadine compounds (WO 00/18764).

Antibodies against CGRP have also been described, and inactive derivatives of CGRP, e.g. CGRP 8-37 which differs from normal CGRP in that it lacks 8 N-terminal amino acids. U.S. Pat. No. 5,935,586 describes the use of CGRP antagonists in therapeutic/cosmetic compositions for treating diseases of the skin, in particular, lichens, prurigos, pruriginous toxidermas and severe pruritus. U.S. Pat. No. 5,932,215 describes similar use for treating skin redness, rosacea and discrete erythema.

Increased CGRP Activity at the Active Edge of a Psoriatic Lesion

Example 11 describes measuring CGRP using ELISA technique. Example 13, which differs from Example 11, describes detecting CGRP activity using immunohistochemical methods, specifically immunohistochemistry of neuropeptides at an active edge. An active edge of a psoriatic lesion is defined as the area of a psoriasis lesion, as seen in FIG. 8, where there is significantly increased blood flow as measured by laser Doppler flowmetry. The active edge also shows early histological psoriasis changes. Example 13 confirms that CGRP activity is increased in normal looking skin outside the visible psoriatic lesion. This supports CGRP activity being responsible for psoriasis, enabling more effective treatment by applying CGRP antagonist(s) to normal looking skin outside the lesion, where access to the intradermal layers is easier than through the fully thickened scaly lesion. This demonstrates that the area outside the visible psoriatic lesion, the so called pre-psoriatic rim, is the most active source of CGRP and thus will be effected when treating with a CGRP antagonist.

Pre-Psoriatic Rim Treatment of Psoriasis and Local Neural Transport

Determining that the pre-psoriatic rim has elevated CGRP activity is informative, but insufficient to predict that successful application of a medicament to the pre-psoriatic rim will be sufficient to affect, i.e., to treat, the whole lesion. The inventor's successful treatment by pre-psoriatic rim application of a medicament to treat psoriasis was explained by observation of interadermal pressurized air canals that facilitate delivery from the pre-psoriatic rim area to the skin underlying the lesion where the pathology is most severe.

Drugs, neural components such as neuropeptides, and hormones, e.g. adrenaline, CGRP, Substance-P, are rapidly transported from one location to another through channels in the deep dermis. This can be seen when lidocaine with adrenaline, for local anesthesia, is injected into the skin, e.g., making the spread of vasoconstriction occur in only few minutes from the sole to the ankle (FIG. 7). This transport system collapses because of the pressure drop when a skin biopsy is taken, making it difficult to observe as it will become almost indistinguishable from adjacent layers when it has been depressurized.

The most used model to measure drug penetration uses dead skin (Franz cells) and according to the theory, this system does not represent normal function skin. Why drugs or other components are more easily able to treat the psoriasis lesion via normal skin around the lesion is because this system is under the lesion and can be reached more easily from the sides. Psoriasis affects the vessels in the surface and the epidermis; the inflammation is also mostly located in that area, assuming the transport system lies underneath the superficial dermis. It is very difficult to reach the deep dermis going through thick, scaly, and hyperperfused skin. This depth can likely be reached via normal hair follicles around psoriasis lesions.

Psoriasis is a complex, multifactorial, lifelong disease of unknown etiology. The two main histological factors of psoriasis are epidermal hyperplasia and inflammatory cell infiltrates in the dermis (Nickoloff and Nestle. Recent insights into the immunopathogenesis of psoriasis provide new therapeutic opportunities. J Clin Invest, 113(12):1664-1675, 2004).

Until the 1980s the primary pathology of psoriasis was considered to be epidermal hyperplasia. Studies over the last decades have on the contrary indicated that psoriasis is mediated by immunological mechanisms. As a result the T-cell theory has been proposed, which implies that psoriasis is a disorder of abnormal keratinocyte proliferation caused by activated T-lymphocytes (Christophers, The immunopathology of psoriasis. Int Arch Allergy Immunol, 110(3):199-206, 1996). This role of T-cells was first suggested in 1976 after the observation that psoriasis lesions cleared on cyclosporine treatment (Krueger et al. Inflammatory and immune cell function in psoriasis: II. monocyte function, lymphokine production. J Invest Dermatol, 71(3):195-201, 1978).

The concept of cutaneous neuroimmunology in psoriasis is relatively recent. Farber et al. were the first to propose a possible role for neuropeptides in the pathogenesis of psoriasis in 1986 (Farber et al. Stress, symmetry, and psoriasis: possible role of neuropeptides. J Am Acad Dermatol, 14(2 Pt 1):305-311, 1986). Subsequently other investigators observed up-regulation of various neuropeptides in psoriasis lesions (Naukkarinen et al. Quantitative analysis of contact sites between mast cells and sensory nerves in cutaneous psoriasis and lichen planus based on a histochemical double staining technique. Arch Dermatol Res, 283(7):433-437, 1991; Naukkarinen et al. Quantification of cutaneous sensory nerves and their substance p content in psoriasis. J Invest Dermatol, 92(1):126-129, 1989, Abstracts for the 1992 Annual Meeting of the European Society for Dermatological Research. London, Apr. 4-7, 1992. J Invest Dermatol, 98(4):503-546, 1992), however, the opposite has also been reported (Pincelli et al. Substance p is diminished and vasoactive intestinal peptide is augmented in psoriatic lesions and these peptides exert disparate effects on the proliferation of cultured human keratinocytes. J Invest Dermatol, 98(4):421-427, 1992).

Neuropeptides and their receptors have been detected in normal human skin and adjacent epithelial tissues. In the skin, neuropeptides are involved in sensory innervation, secretory glands, epidermal growth, regulation of blood flow, and immune cell trafficking. Neuropeptides are important in wound healing and tissue repair (Wollina, The effect of neuropeptides on wound healing in vitro and in vivo, Hautarzt, 43(10):616-620, 1992).

Large clinical studies have demonstrated that stress plays an important role in the onset or exacerbation of psoriasis (Park and Youn. Factors influencing psoriasis: an analysis based upon the extent of involvement and clinical type. J Dermatol, 25(2):97-102, 1998). Symmetry of lesions and the well-documented Koebner's phenomenon where psoriasis appears at the point of injury are among the cardinal clinical features of psoriasis. A study showing psoriasis resolving on a knee after surgery with sensory loss due to nerve damage, suggests that nerves or neurotransmitters might initiate the psoriasis lesion (Farber et al. The role of cutaneous sensory nerves in the maintenance of psoriasis. Int J Dermatol, 29(6):418-420, 1990). Besides theses clinical observations, histological and electron microscopic studies have shown an accelerated turnover of neural elements and denser innervation in mature psoriatic lesions (Weddell et al., Psoriatic Skin, Arch Dermatol, 91:252-266, 1965). In addition, psoriasis has been linked to the early wound healing process both histologically and through the Koebner's phenomena (Foster et al. Calcitonin gene-related peptide is chemotactic for human t lymphocytes. Ann N Y Acad Sci, 657:397-404, 1992).

The neuropeptide calcitonin gene-related peptide (CGRP) is a 37 amino acid peptide. CGRP acts by stimulating specific CGRP receptors. CGRP is the most prominent neuropeptide in the skin and is also found in other tissues, e.g. bone and joints. CGRP stimulates keratinocyte, i.e., epidermal cell, proliferation (Takahashi et al. Direct effects of cutaneous neuropeptides on adenylyl cyclase activity and proliferation in a keratinocyte cell line: stimulation of cyclic AMP formation by CGRP and VIP/PHM, and inhibition by NPY through g protein-coupled receptors. J Invest Dermatol, 101(5):646-651, 1993) but does not cause irritation or itching (Weidner et al., Acute effects of substance p and calcitonin gene-related peptide in human skin—a microdialysis study. J Invest Dermatol, 115(6):1015-1020, 2000). CGRP is the most potent vasodilating compound known and it is chemotactic and mitogenic for T-cells and neutrophils (Foster et al. Calcitonin gene-related peptide is chemotactic for human t lymphocytes. Ann N Y Acad Sci, 657:397-404, 1992; Cuesta et al. Substance p and calcitonin gene-related peptide increase IL-1 beta, IL-6 and TNF alpha secretion from human peripheral blood mononuclear cells. Neurochem Int, 40(4):301-306, 2002). CGRP increases TNF-alpha secretion from mast cells and TNF-alpha can stimulate CGRP secretion from ganglion neurons (Bowen et al. Tumor necrosis factor-alpha stimulation of calcitonin gene-related peptide expression and secretion from rat trigeminal ganglion neurons. J Neurochem, 96(1):65-77, 2006). CGRP increases various interleukins such as IL1, IL6, and IL8. These mediators are secreted from various cell types like keratinocytes, neutrophils, and lymphocytes (He et al., Calcitonin gene-related peptide induces chemokine interleukine-8 synthesis in human monocytes; Yi and Zhi, 82(2): 131-134, 2002; Foster et al. Calcitonin gene-related peptide is chemotactic for human t lymphocytes. Ann N Y Acad Sci, 657:397-404, 1992; Cuesta et al. Substance p and calcitonin gene-related peptide increase IL-1 beta, IL-6, and TNF alpha secretion from human peripheral blood mononuclear cells. Neurochem Int, 40(4):301-306, 2002). CGRP directly stimulates stem cells in the skin (Dong et al., Calcitonin gene-related peptide regulates the growth of epidermal stem cells in vitro. Peptides, 31(10):1860-1865, 2010). CGRP is a strong inhibitor of Langerhans cells (antigen presenting cells). CGRP is an active neuropeptide early in the skin wound healing process (Onuoha and Alpar, Levels of vasodilators (SP, CGRP) and vasoconstrictor (NPY) peptides in early human burns. Eur J Clin Invest, 31(3):253-257, 2001). UV irradiation causes reduction in the number of CGRP-immunoreactive nerve fibers in the dermis according to study investigating inflammatory process in normal skin (Wallengren and Sundler. Phototherapy reduces the number of epi-dermal and CGRP-positive dermal nerve fibres. Acta Derm Venereol, 84(2):111-115, 2004).

In 1989 Hull et al discovered a growth pattern of psoriasis lesions by detecting an edge of increased blood flow. They used Laser Doppler flowmeter to track increased blood perfusion. This increased blood flow was the growing edge of the psoriasis lesions. By this observation they showed that it was possible to locate areas where very early psoriasis changes were present, days or even weeks before they could be seen by the naked eye (Hull et al. Active and inactive edges of psoriatic plaques: identification by tracing and investigation by laser-doppler flowmetry and immunocytochemical techniques. J Invest Dermatol, 92(6):782-785, 1989).

The hypothesis of the present invention suggests that overrepresentation of calcitonin gene related peptide (CGRP) is responsible for most of the pathological phenomena of psoriasis like hyperproliferation, increased number of T-cells, increased blood flow, and localization of lesions. It can also explain the therapeutic effect of sunlight, and the negative effect of streptococcal infection on psoriasis. Alopecia areata (AA) is a functional hair disease where a lack of CGRP seems to be a causing factor. An inverse relationship between AA and psoriasis has been observed and is described herein. CGRP can be a common factor in both diseases, as it is involved in the use of papillary cells for wound healing and through that route can activate hair follicles in the wound healing process. It is known that psoriasis is a disease connected to the early wound healing process. The observations described herein showing hexagonal structure of psoriasis lesions strongly suggests that the disease involves neural units of sensory innervation. In conclusion, it is a novel hypothesis of the Inventor set forth and supported herein that psoriasis is a disease of neural origin and CGRP is likely to be a key mediator of the disease. According to this hypothesis, it is the regulation of CGRP that is not functioning properly in psoriasis, and consequently, regulation of CGRP by use of a CGRP antagonistic compound is a way of controlling psoriasis.

The present invention describes a novel method for the treatment and prevention of psoriasis by modulating the concentration of CGRP in the body, especially in the skin, e.g., by the use of CGRP antagonists. The invention is supported by the novel observations and descriptions herein that explain psoriasis as a disease of neurological origin for which CGRP s a key mediator.

The invention is based on the notion that by changing the level of CGRP, at least in the psoriatic. lesions, such as by blocking the activity of CGRP, the disease can be treated and/or prevented. This may be effected by the administration of CGRP antagonist compounds, or by administering tryptase or other compounds affecting the level of CGRP.

In one embodiment, an inventive composition such as a CGRP antagonist is topically administered to the pre-psoriatic rim, the area outside the visible psoriatic lesion. This method of administration is further strengthened with research data showing increased CGRP activity at the pre-psoriatic rim of a psoriasis lesion. The pre-psoriatic rim is in a normal looking skin outside of the lesion and is confirmed by increased blood flow measured using laser Doppler technology.

DETAILED DESCRIPTION

As mentioned, the current invention relates to methods for treating, remedying or preventing psoriasis by the use of CGRP antagonist compounds. To date it has not been envisaged to treat psoriasis with CGRP antagonists. Accordingly, the present invention features the use of at least one CGRP antagonist compound for the treatment of psoriasis.

CGRP antagonist in this context represents any molecule, whether organic or inorganic, which is capable of reducing the level of active CGRP, e.g., by effecting inhibition of the receptor binding of CGRP or of effecting inhibition of the synthesis and/or release of CGRP by nerve fibers, or enhancing the breakdown of active CGRP. Thus tryptase active polypeptides falls within this category as defined herein as they can affect the level of CGRP by cleavage of the peptide, as well as compounds stabilizing tryptase, such as heparin. As mentioned above, many compounds have been recently developed that fulfill these criteria and thus are useful in the current invention.

Treatment in this context indicates any form of therapy that cures or relieves at least partially the symptoms of the disease, for at least a period of time, remedying the disease indicates herein full or partial relief of psoriasis symptoms.

Microdialysis is a method for tissue fluid sampling. It has been used both in the skin and other tissues.

Laser-Doppler flow measurement is a technique for measuring localized superficial blood flow in the skin.

In a first aspect, the invention provides a method of treating psoriasis in a subject comprising administering to the subject a therapeutically effective dose of at least one CGRP antagonist compound in a pharmaceutically acceptable formulation. A therapeutically effective dose will depend on the particular compound selected but is typically in the range of about 0,00001% to. 5% of the total weight of a pharmaceutical composition being used for said treatment, preferably in the range of about 0,0001% to 2.5% of weight, such as in the range of 0,001 to 1% of weight, or in the range of 0,001 to 0.1% of weight.

A suitable pharmaceutically acceptable formulation may be formulated according to conventional pharmaceutical methods, depending on the compound being selected and the intended route of administration, as discussed further below.

The method according to the invention includes both systemic and/or local treatment. Accordingly, the compositions for use according to the invention may be administered orally, nasally, rectally, pulmonary, buccally or via subcutaneous: intravenous or intramuscular injection in order to reach the lesions from a distal administration, or by administering the composition locally, such as topically, dermally, intradermal or subcutaneously, or via dermal or subcutaneous infusion such as through microdialysis. However, presently preferred embodiments comprise topical administration. In one embodiment, the method comprises administration to the pre-psoriatic rim. As can be seen in Example 13, this method of applying a medicament to the pre-psoriatic rim is based on ground breaking research done by the Applicant. The research illustrates that the psoriatic activity is occurring outside the lesion, and more specifically at the pre-psoriatic rim in agreement with Example 11, where the CGRP activity is found to be increased. These results show that treatment at the active source of CGRP is most likely to be successful in comparison to direct application to the lesion itself.

It will thus be readily understood from the description herein, that the invention provides in a related aspect, the use of a CGRP antagonist compound for the manufacture of a medicament for treating, remedying or preventing psoriasis in a subject in need thereof. Such medicaments are preferably such compositions as are disclosed herein.

However, in another aspect, the invention provides a method to reduce hair growth by the application of a CGRP antagonist compound such as defined above. This aspect stems from the novel theory that CGRP regulates the hair growth cycle, as discussed above. In preferred embodiments of the invention, these methods comprise the topical or dermal application of medicaments such as a cream, ointment, gel, paste, iontopophoresis system, liquid or lotion, to the area where hair growth reducing effect is wanted.

The topical formulations according to the invention comprise an active ingredient together with one or more pharmaceutically acceptable carrier and/or excipient compounds and optionally one or more therapeutically active ingredient.

Formulations suitable for topical administration may be formulated into any pharmaceutical form normally employed for such an application, these include liquid or semi-liquid preparations including lotions, creams, pastes, ointments, liposomes, gels, such as for iontopophoresis, suspensions and emulsions, including oil/water (w/o), w/o, o/w/o, w/o/w emulsions or microemulsions. They may suitably be obtained by mixing the active ingredient in finely-divided or powdered form, alone or in solution or suspension in an aqueous or non-aqueous fluid, with the aid of suitable machinery, with a hydrophobic or hydrophilic basis. The basis may comprise hydrocarbons such as hard, soft or liquid paraffin, glycerol, waxes (e.g., beeswax, carnauba wax), metallic soap, a mucilage, an oil of natural origin such as corn, almond, castor, or olive oil, mineral oils, animal oils (perhydroxysqualene); or a fatty acid such as stearic or oleic together with an alcohol such as ethanol, isopropanol, and propylene glycol. The formulation may include any suitable surface active agent such as an anionic, cationic, or non-ionic surfactant such as sorbitan esters or polyoxyethylene derivatives thereof. Suspending agents such as natural gums; cellulose derivatives or inorganic materials such as silicaceous silicas may also be included. The formulations may additionally comprise absorbtion promoters, stabilizers, e.g. protein stabilizing agents, known in the art.

Known CGRP antagonist compounds which are useful in the current invention include 4-sulfinyl benzamide compounds such as those disclosed in WO 98/56779, 3,4-dinitrobenzamide compounds such as those disclosed in WO 98/09630, benzamidazollnyl piparadine compounds such as disclosed in WO 00/18764, CGRP derivatives including CGRP 8-37, having the sequence VTHRLAGLLSRSGGMVKSNFVPTNVGSKAF (SEQ ID NO:1) or VTHRLAGLLSRSGGVVKNNFVPTNVGSKAF (SEQ ID NO: 2), and anti-CGRP antibodies. An interesting compound described in the art a non-peptide molecule produced by Boehringer Ingelheim, termed BIBN4096BS (see, Wu et al., Biochem. Soc. Trans. 2002, August 30(4): 468-473).

Compounds that are believed to have a CGRP antagonist activity and thus being candidate compounds for use according to the present invention include:
- (±)-4-[(2-chlorophenyl)sulfinyl]-N-methyl-N-(2-methylphenyl)-3-nitrobenzarnide;
- (+)-4-[(2-chlorophenypsulfinyl]-N-methyl-N-(2-methylphenyl)-3-nitrobenzamide;
- (−)-4-[(2-chlorophenyl)sulfinyl]-N-methyl-N-(2-methylphenyl)-3-nitrobenzamide;
- (±)-4-[(4-chlorophenyl)sulfinyl]-N-methyl-N-(2-methylphenyl)-3-nitrobenzamide;
- (±)-N-methyl-N-(2-methylphenyl)-44(1-oxido-2-pyridinyl)sulfinyl]-3-nitrobenzamide;
- (±)-N-methyl-N-(2-methylphenyl)-3-nitro-4-(2-thiazolylsulfinyl)benzamide;
- (±)-N-methyl-N-(2-methylphenyl)-4-[(5-methyl-1,3,4-thiadiazol-2-yl)sulfinyl]-3-nitrobenzamide;
- N[3-[(diethylamino)carbonyl]propyl]-N-(-2ethylphenyl)-3-nitro-4-(2-thiazolylsulfinyl)benzamide;
- 1-[4-amino-3,5-dibromo-N-[[4-(3,4-dihydro-2(1H)-oxoquinazolin-3-yl)-1-piperidinyl] methylsulfonyliminomethyl]-D-phenylalanyl]-4-(1-piperidinyl)-piperidine;
- 1-[4-amino-3,5-dibromo-N-[[4-(3,4-dihydro-2(1H)-oxoquinazolin-3-yl)-1-piperidinyl] cyanoiminomethyli-D-phenylalanyl]-4-(1-piperidinyl)-piperidine;
- 1-[4 amino-3,5-dibromo-N-[[4-(3,4-dihydro-2(1H)-oxoquinazolin-3Ly1)-1-piperidinyl] phenylsulfonyliminomethyI]-D-phenylalanyl]-4-(1-piperidinyl)-piperil-[3,5-dibromo-N-[[4-(3,4-dihydro-2(1H)-oxoquinazolin-3-yl)-1-piperidinyllcyanoinninomethyl J-D-tyrosyl]-4-(1-piperidinyl)-piperidine;
- 1-[N2-[3,5-dibromo-N-[[4-(3,4-dihydro-2(1H)-oxoquinazolin-3-yl)-1-piperidinyl] methylsulfonyliminomethyll-D-tyrosyli-L-lysyl]-4-(4-pyridinyl)piperazine;
- 1-[N2-[3,5-dibromo-N-[[4-(3,4-dihydro-2(1H)-oxoquinazolin-3-yl)-1-piperidinyl] phenylsulfonyliminomethylj-D-tyrosyll-L-lysyl]-4-(4-pyridinyl)piperazine;
- 1-[4-amino-3,5-dibromo-N-[[4-(3,4-dihydro-2(1H)-oxoquinazolin-3-yl)-1-piperidinyl] cyanoiminomethyli-D-phenylalanyl]-4-(1-methyl-4-piperidinyl)-piperidine;
- 1-[4-bromo-N-[[4-(3,4-dihydro-2(1H)-oxoquinazolin-3-yl)-1-piperidinylicyanoiminomethyl]-3,5-dimethyl-D,L-phenylalanyl]-4-(1-piperidinyl)-piperidine;
- 1-[3,5-dibromo-N-[[4-(3,4-dihydro-2(1H)-oxoquinazolin-3-yl)-1-piperidinyl] cyanoinninomethyl-D-tyrosyl]-4-(4-pyridinyl)piperazine;
- 1-[4-amino-3,5-dibromo-N4[4-(3,4-dihydro-2(1H)-oxoquinazolin-3-yl)-1-piperidinyl] cyanoiminomethyll-D-phenylalanyl]-4-(4-pyridinyl)piperazine;
- 1-[3,5-dibromo-N-[[4-(3,4-dihydro-2(1H)-oxoquinazolin-3-yl)-1-piperidinyl] cyanoiminomethyl]-D-tyrosyl]-4-(1-methyl-4-piperidinyl)-piperidine;
- 1-[3,5-dibromo-N-[[4-[3,4-dihydro-2(1H)-oxoquinazolin-3-yl]-1-piperidinyl] cyanoinninomethylFD-tyrosyl]-4-(4-methyl-1-piperazinyl)piperidine;
- 144-bromo-N-H4-(3,4-dihydro-2(1H)-oxoquinazolin-3-yl)-1-piperidinyl] cyan oiminomethyl]-3,5-dimethyl-D,L-phenylalanyl]-4-(1-methyl-4-piperidinyl)piperidine;
- 144-amino-3,5-dibromo-N-[[441,3-dihydro-4-phenyl-2 (2H)-oxoimidazol-1-yll-1-piperidinyl]cyanoiminomethyn-D-phenyl-alanyl1-4-(4-methyl-1-piperazinyl)piperidine;
- 1-[4-amino-3,5-dibromo-N-[[4-(2,3,4,5-tetrahydro-2(1H)-oxo-1,3-benzodiazep in-3-yl)-1-piperidinyl]cyanoimi-nomethyll-D-phenylalanyl1-4-(4-methyl-1-piperazinyl)piperidine;
- 1-[4-amino-3,5-dibromo-N-[[4-(2,4-dihydro-5-phenyl-3 (3H)-oxo-1,2,4-triazol-2-yl)-1-piperidinyllcyanoiminomethyll-D-phenylalanyl]-4-(1-piperidinyl)-piperidine;
- 1-[4-amino-3,5-dibromo-N-[[4-(2,3,4,5-tetrahydro-2(1H)-oxo-1,3-benzodiazep in7-3=yl);
- 71-piperidinyficyanoiminomethyli-D-phenylalanyl]-4-(1-piperidinyl)-piperidine;
- 1-[3,5-dibromo-N-[[4-(2,4-dihydro-5-phenyl-3 (3H)-oxo-1,2,4-triazol-2-yl)-1-piperidinylicyanolminomethyll-D-tyrosyl]-4-(1-piperidinyl)-piperidine;
- 143,5-dibromo-N-R4-(2,3,4,5-tetrahydro-2(1H)-oxo-1,3-benzodiazepin-3-yl)-1-piperidinyl]cyanoiminomethyll-D-tyrosyl]-4-(1-piperidinyl)-piperidine;
- 1-[3,5-dibromo-N4 [4-(2,4-dihydro-5-phenyl-3 (3H)-oxo-1,2,4-triazol-2-yl)-1-piperidinyncyanoiminomethylFD-tyrosyl]-4-(1-methyl-4-piperidinyl)piperazine;
- 1-[3,5-dibromo-N-[ [4-(2,3,4,5-tetrahydro-2(1H)-oxo-1,3-benzodiazepin-3-yl)-1-piperidinyncyanoiminomethyl]-D-tyrosyl]-4-(1-methyl-4-piperidinyl)piperazine;
- 1-[4-amino-3,5-dibromo-N4 [4-(2,4-dihydro-5-phenyl-3 (3H)-oxo-1,2,4-triazol-2-yl)-1-piperidinyl]cyanoiminomethyl]-D-phenylalanyl]-4-(1-methyl-4-piperidinyl)piperazine;

1-[4-amino-3,5-dibromo-N-[[4-(2,3,4,5-tetrahydro-2(1H)-oxo-1,3-benzodiazep in-3-yl)-1-piperidinylicyanoiminomethyl]-D-phenylalanyl]-4-(1-methyl-4-piperidinyl)piperazine;

143,5-dibromo-N-H4-(3,4-dihydro-2(1H)-oxoquinazolin-3-yl)-1-piperidinyl] cyanoiminomethyl]-4-methyl-D,L-phenylalanyl1-4-(1-methyl-4-piperidinyl)-piperidine;

1-[3,5-dibromo-N-[[4-(3,4-dihydro-2(1H)-oxoquinazolin-3-yl)-1-piperidinyl] cyanoiminomethyl]-4-methyl-D,L-phenylalanyl]-4-(1-piperidinyl)-piperidine;

1-[3,5-dibromo-N-[[4-(3,4-dihydro-2(1H)-oxoquinazolin-3-yl)-1-piperidinyl] cyanoiminomethyl]-4-methyl-D,L-phenylalanyl]-4-(4-pyridinyl)piperazine;

144-amino-3,5-dibromo-N4 [4-11,3-dihydro-2(2H)-oxoimidazo[4,5-c] quinolin-3-yl]-1-piperidinyl]cyanoiminomethyl]-D-phenylalanyl]-4-(1-piperidinyl)piperidine;

1-[4-amino-3,5-dibromo-N-[[4-(7-methoxy-2,3,4,5-tetrahydro-2(1H)-oxo-1,37benzodiazepin-3-yl)-1-piperidinyl] cyanoiminomethyl]-D-phenylalanyl]-4-(1-piperidinyl)-piperidine, 144-amino-3,5-dibromo-N[[4-(5,7-dihydro-6-oxodibenzo[d,f] [1,3]-diazepin-5-yl)-1-piperidinyncyanoiminomethyl]-D-phenylalanyl]-4-(1-piperidinyl)-pipendinel 1-[4-amino-3,5-dibromo-N-[[4-(7-methoxy-2,3,4,5-tetrahydro-2(1H)-oxo-1,3-b enzodiazepin-3-yl)-1-piperidinylicyanoiminomethyll-D-phenylalanyl]-4-(1-met hyl-4-piperidinyl)piperazine;

144-amino-3,5-dibromo-N-[[441,3-dihydro-2(2H)-oxo-imidazo[4,5-c]quinolin-3-yl]-1-piperidinyl]cyanoiminonnethyl]-D-phenylalanyl]-4-(1-methyl-4-piperidinyl)piperazine, 1-[4-amino-3,5-dibromo-N-[[4-(2,3,4,5-tetrahydro-2(1H)-oxo-1,3-benzodiazep in-3-yl)-1-piperidinyl] sulfonyli-D-phenylalanyl]-4-(1-methyl-4-piperidinyl)piperazine;

1-[3,5-dibromo-N-[[4-(7-methoxy-2,3,4,5-tetrahydro-2(1H)-oxo-1,3-benzodiaz epin-3-yl)-1-piperidinylicyanoiminomethyll-D-tyrosyl]-4-(1-piperidinyl)piperidine;

1-[3,5-dibromo-N-[[4-(7-methoxy-2,3,4,5-tetrahydro-2(1H)-oxo-1,3-benzodiaz epin-3-yl)-1-piperidinyl]cyanoiminomethyll-D-tyrosyl]-4-(1-methyl-4-piperidinyl)piperazine;

1-[3,5-dibromo-N-[[4-[1,3-dihydro-2(2H)-oxoimidazo[4,5-c] quinolin-3-yl1-1-piperidinyl]cyanoiminomethyll-D-tyrosyl]-4-(1-piperidinyl)piperidine;

143,5-dibromo-N-[[441,3-dihydro-2(2H)-oxoimidazo[4,5-c] quinolin-3-yl]-1-piperidinyl]cyanoiminomethyl]-D-tyrosyl]-4-(1-methyl-4-piperidinyl)piperazine;

144-amino-3,5-dibronno-N4[4-(7-methoxy-2,3,4,5-tetrahydro-2(1H)-oxo-1,3-benzodiazepin-3-yl)-1-piperidinyl] cyanoiminomethyl-D-phenylalanyl]-4-(4-methyl-1-piperazinyl)-piperidine;

144-amino-3,5-dibromo-N-[[441,3-dihydro-2(2H)-oxoimidazo[4,5-c]quinolin-3-yl]-1-piperidinylicyanoiminomethylFD-phenylalanyl]-4-(4-methyl-1-piperazinyl)piperidine;

and pharmaceutically acceptable salts thereof.

It is further contemplated that indirect inhibitors of CGRP activity may be useful according to the invention. These include the capsaicin blocker capzaezine, as CGRP is postulated to be under the influence of capsaicin through the vanillin receptor. Other such indirect inhibitors include Histamine H3-receptor agonists such as Imetit which can downregulate CGRP.

In a useful embodiment of the invention, the pharmaceutical composition comprising a CGRP antagonist compound is administered for treatment of psoriasis in combination with another treatment form, such as UVB treatment which is performed with standard methods in the art.

In another aspect of the invention, a method is provided for identifying a candidate compound for use in a medicament for treating psoriasis. The method comprises—the steps of obtaining a compound suspected of binding to a CGRP receptor; adding the compound at varying concentrations such as in the range of about 0.1 µM to 1 mM to samples comprising CGRP receptors and incubating for a suitable time; adding labeled CGRP peptide to the incubated samples (e.g., radiolabeled, such as by iodine125, though other labeling methods well known in the art are applicable as well); determining the binding of the labeled CGRP peptide to the CGRP receptor in said samples with varying concentration of the candidate compound; and determining the binding. affinity of the compound to the CGRP receptor; whereby a compound that is determined to bind the CGRP receptor is identified as a candidate compound for use in a medicament for treating psoriasis. An embodiment of the method according to the invention is described in detail in Example 10.

In one embodiment of the method said samples comprise live cells having surface bound CGRP receptors. In certain embodiments said samples comprise cell membrane preparations.

In one embodiment, a method for treating psoriasis comprises topically administering a described composition, e.g. a composition comprising a CGRP antagonist, to an area adjacent but not directly on a psoriatic lesion, i.e., pre-psoriatic rim administration, to treat psoriasis, as Example 12 discloses.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following examples illustrate embodiments of the inventive method.

EXAMPLE 1

Case Study: Possible Involvement of Neuropeptidergic Sensory Nerves in AA

A recent study by R. Rossi et al. (Rossi, R. et al. Neuroreport, 8, 1135-1138 1997) indicated that patients with AA have lower basal blood flow. It was further shown that CGRP and SP (substance P) levels but not VIP (vasoactive intestinal peptide) are decreased in scalp biopsies of patients affected by AA. Reaction to stimuli is altered, such that a greater and more prolonged vasodilation in response to intradermal CGRP is observed in alopecic scalp than in controls. This is suggested by the authors of the study to indicate CGRP receptor hypersensitivity, due to a previous reduction in the amount of the neuropeptide present.

EXAMPLE 2

Clinical Observation of a Patient with AA and Psoriasis

Figure 1A:
FIGS. 1a and 1b show images that depict the scalp of a patient with alopecia aerata and psoriasis.
Figure 1B:

A clinical observation of a Down's syndrome patient with AA and psoriasis showed that the patient had AA covering an area from one ear to the other through his occipital region. His whole scalp was covered with psoriasis except for the area where he had AA (see FIGS. 1a and 1b). In those areas the scalp was clinically normal. The patient had psoriasis on his elbows and a strong family history of psoriasis.

The observation strongly indicates that there is an inverse relationship between the two diseases, which has to my knowledge not been described before. In conjunction with the results of Example 1 that CGRP levels are lower in AA areas, this further supports the notion that CGRP is a causative agent in psoriasis.

EXAMPLE 3

Clinical Observation of Psoriasis Patients Treated with UVB Therapy

Patients receiving UVB treatment according to standard clinical practice were observed and interviewed. It was noticed that several patients experienced transient worsening of psoriasis after their first treatment sessions, in the very first days after initiating treatment, before they begin to get better. Worsening was defined as flare-up or increased size of existing lesions or appearance of new ones.

Out of 95 patients interviewed, 38 said they had experienced worsening of their psoriasis. 21 got new lesions, most often lasting for 1 or 2 days. These lesions were often described as small, thin and red macules. 17 patients noticed a short worsening period of already existing psoriasis lesions. These symptoms were noted typically within 24-48 hours after first treatment. All, patients, however, benefited from the treatment, i.e., received overall improvement of psoriasis over a longer time.

I postulate that in the beginning of the treatment, increased CGRP is a normal reaction to UV radiation and heat trauma. (This has been observed experimentally in rats, see Gillardon et al. Neurosci. Lett. 1991 Apr. 1; 124(2):144-7) As the stimulus is ongoing, it is conceivably beneficial for the body to increase the specific defense mechanism and decrease cell turnover, by down-regulation of CGRP. In such a way the risk of mutation and skin cancer may be reduced. Thus, the increased CGRP levels in skin during beginning of UVB therapy enhances the patient's psoriasis symptoms, before the healing effect of the therapy sets in.

EXAMPLE 4

Study of Psoriasis Pattern and Location

Figure 2A:
FIGS. 2a and 2b show a psoriasis pattern on legs of patients.
Figure 2B:
Figure 3:
FIG. 3 shows psoriasis lesions on a finger.

Psoriasis lesions on a number of patients have been carefully studied to analyze patterns of the lesions. A hexagonal pattern can be observed on many patients, see FIGS. 2-3. Such pattern has not been described before. It is postulated that the pattern is a representation of neurological units. The exact structure of the nerve innervations in the skin has never been described in detail.

EXAMPLE 5

Herpes Zoster Pattern

Figure 4:
FIG. 4 is an image showing Herpes zoster lesions.

The pattern of Herpes Zoster lesions has been studied. It is noted that such patterns also show hexagonal pattern (FIG. 4). Herpes Zoster, a viral nerve infection, has a known neurological connection, and therefore the fact that hexagonal patterns are observed in both Herpes Zoster and psoriasis supports that such patterns are representations of neurological units.

EXAMPLE 6

Psoriasis Lesions Formed after Skin Injury

Figure 5:
FIG. 5 shows psoriasis lesions formed after skin injury.

A psoriasis patient developed psoriatic lesions where his skin had been scratched or injured. It is frequently observed that lesions appear where the skin has been injured, this is called the Koebner's phenomenon. I observed that the lesions, showed a fine hexagonal pattern (see FIG. 5). It can thus be concluded that whereas the location of the "straight-line" lesions is caused by the injury to the skin, the finer structure-pattern comprising semi-circles or hexagons, is a strong indication of the disease's neural connection. It can further be observed in FIG. 5 that the sizes of the hexagons are interrelated such as e.g. the broader lines are comprised of hexagons that are comprised of the smaller hexagonal units of the finer lines. This propagation indicates that neural units of fixed size are activated in psoriasis. This has never been suggested before in the prior art.

EXAMPLE 7

Study of Alopecia Areata Pattern

Figure 6A:
FIGS. 6a and 6b show patterns of alopecia aerata on the scalp of a patient.
Figure 6B:
Figure 7:
FIG. 7 shows the spread of vasoconstriction when lidocaine and adrenaline, local anaesthesia, is injected into the skin.

FIGS. 6a and 6b of the scalp of a patient with Alopecia areata (AA) reveals that Alopecia spots display non-circular forms resembling hexagonal shape. In light of the discussion herein regarding the relationship between AA and psoriasis, the indication that AA also shows patterns indicative of neural factors further support the notion of psoriasis being a neurological disorder.

EXAMPLE 8

Case Study: Topical Immunotherapy for Alopecia Areata

Orecchia et al. (Orecchia, G. et al. Dermatologica 1990, 180, 57-59) describe treatment of AA with SABDE (squaric acid dibutylester), a topical sensitizer. A patient who received the treatment developed psoriasis at the same spot where he got hair regrowth. Hairs on the psoriatic plaques were the last to fall off when the disease progressively worsened after treatment, to Alopecia Universalis.

As discussed in the detailed description, to activate keratinocytes from hair follicles which act as reserve cells, CGRP can turn the hair in resting phase (telogen phase) into active phase (anagen phase). When the body is exposed to antigen in very small quantities (as topical immunotherapy) CGRP is released to stop the process of delayed type hypersensitivity (DTH) to evolve. I believe that is the reason why SABDE and DPCP are effective in treatment of Alopecia Aerata. This mechanism involving CGRP as a downregulator of DTH and actor in early wound healing which is able to turn hair follicles from telogen to anagen phase explains why there is an inverse relationship between psoriasis and AA, as demonstrated in the Example 1.

EXAMPLE 9

Lotion for Treating Psoriasis

A lotion for treatment and/or prevention of psoriasis by topical administration may be prepared as follows:

A suitable compound is selected, from those disclosed in the description or a compound identified with the method of Example 10 percent lotion is prepared as follows: about 0.1 to 0.5 g of the compound is dissolved in ethanol (6 ml), and the solution is admixed with a water-in-oil lotion (95 g) prepared from mineral oil, cottonseed oil, isopropyl palmitate and water with a surfactant such as sorbitan sesquioleate. The ingredients in the water-in-oil lotion are present for example in 10:10:5:70:5 parts by weight respectively.

EXAMPLE 10

Screening for Antagonistic Compounds

A method is described in WO 98/56779 to screen for compounds that hinder the CGRP receptor from binding CGRP. Thus, the method will identify compounds that are likely to be useful for the current invention.

Briefly, the selected test compounds are assayed for the inhibition of $[^{125}I]$ CGRP (from Amersham, Chicago, Ill.). SK-N-MC cells (American Type Culture Collection, Rockville, Md.) are grown in Minimum Essential Medium ("MEM") containing fetal calf serum (10%). Cells are grown in T-150 flasks or Costar® multiwell plates and maintained at 37° C. in a 90% humidified incubator with an atmosphere of 5% $CO_2$ and 95% air.

The cells are homogenized in 5 mM Tris-HCl pH 7.4, 10 mM Na-EDTA and the homogenate centrifuged at 48,000 g for 20 min at 4° C. The pellet is re-suspended in 20 mL Na-HEPES pH 7.4, 10 mM $MgCl_2$ and recentrifuged. The membrane pellets are re-suspended in the same buffer and stored frozen at −70° C. The protein concentration is measured by the Pierce BCA method using BSA (Bovine serum albumin) as a standard.

The $[^{125}I]$CGRP receptor binding assay is performed using a buffer of 20.mM Na-HEPES pH 7.4, 10 mM $MgCl_2$, 0.05% BSA and 0.1 mg/mL bacitracin. The membranes (50 pg/mL) are incubated with various concentrations (such as in the range of about 1 pM and 1 mM) of the test compounds and 40 pM $[^{125}I]$CGRP in a total volume of 500 pL for 60 min at 25° C. The reaction is terminated by addition of 2 mL ice-cold 0.9% NaCl, followed by rapid filtration through Skatron Filtermates pre-soaked in 0.5% polyethylenimine (PEI). The filters are rinsed twice with 2 mL of cold 0.9% NaCl and the radioactivity counted in a gamma counter. The binding data is analyzed with conventional ligand-binding calculations and programs, such as the LIGAND 2 program.

EXAMPLE 11

Measurement of CGRP in Edges Surrounding Psoriasis Lesions

Laser Doppler blood flow measurement was used to measure blood flow in normal skin surrounding psoriasis lesions to determine the location of the active edge of psoriasis lesions. It is known that psoriasis lesions grow directionally, i.e., have a growing or active edge (see, Cunliff et al. J. Invest. Dermatol. 1989, 92(6):782-5). CGRP levels were measured in both the active edge and the inactive (opposite) edge in two subjects having psoriasis lesions. Initial results indicate that CGRP levels are increased in the pre-psoriatic rim as compared to the normal skin on the opposite side outside the lesion. The experiment was conducted by the use of microdialysis equipment for tissue fluid sampling with a 15 kDa cutoff probe; both the active and inactive edge were sampled for a total of 165 min. each sample to obtain a volume of 165 pL in each sample. Neuropeptide CGRP concentration was measured with ELISA. Tissue biopsies from the sampled skin locations were taken after the tissue fluid sampling. At the active edge increased blood flow was observed indicated by increased capillary blood vessels indicated by increased number of capillary loops in the papillary dermis, which also were dilated. No epidermal hyperplasia or T-cell activation were found.

The results strongly indicate that increased concentration in CGRP level in the skin is a very early event in the development of psoriasis. This supports that failure in regulating the CGRP level (i.e. an enhanced CGRP level) could be a causative factor in the psoriasis disease.

EXAMPLE 12

Pre-Psoriatic Rim Administration and Treatment of Psoriasis

A selected compound as described herein or identified with the method of Example 10 is prepared as by dissolving about 0.1 to 0.5 g of the compound in ethanol (6 ml), then the solution is admixed with a water-in-oil lotion (95 g) prepared from mineral oil, cottonseed oil, isopropyl palmitate and water with a surfactant such as sorbitan sesquioleate. The ingredients in the water-in-oil lotion are present, e.g., in 10:10:5:70:5 parts by weight respectively. In one embodiment, 0.10 g of the compound is dissolved in 80.0 g aqueous 20.0 mM acetic acid buffer pH 4.0, containing 4.0 g of glycerol, 7.0 g of sorbitol and 0.1 g of methylparaoxybenzoate. In one embodiment, the ingredients in the aqueous phase are present in 84.875:8.75:6.25:0.125 parts by weight respectively. In one embodiment, the oil phase is 20.0 g and consists of 0.5 g of polysorbat 80, 6.0 g of cetosteraryl alcohol, 6.0 g of paraffin oil and 7.5 g of glycerolmonostearate 40-50 (2.5:30:30:37.5 parts by weight respectively). In one embodiment, the oil phase is heated up to 70° C. and mixed in an emulsion machine for 2 minutes with 65° C. aqueous phase to prepare an oil-in-water emulsion and cooled to room temperature under manual stirring. In one embodiment, 0.10 g of the compound is dissolved in 99.0 g aqueous 20.0 mM acetic acid buffer pH 4.0, containing 0.1 g of methylparaoxybenzoate. 1.0 g of Hydroxypropylcellulose (Klucel® HF hydroxypropylcellulose) is added to the solution and stirred until uniform fully hydrated gel forms (30 minutes).

In one embodiment, a composition for topical administration was prepared using the peptide CGRP8-37 in a topical formulation at 20 µg/g. The effective range of the peptide in the composition can be between 0.00001 µg/g to 1 g/g, depending on formulation and measured penetration parameters.

Figure 8:
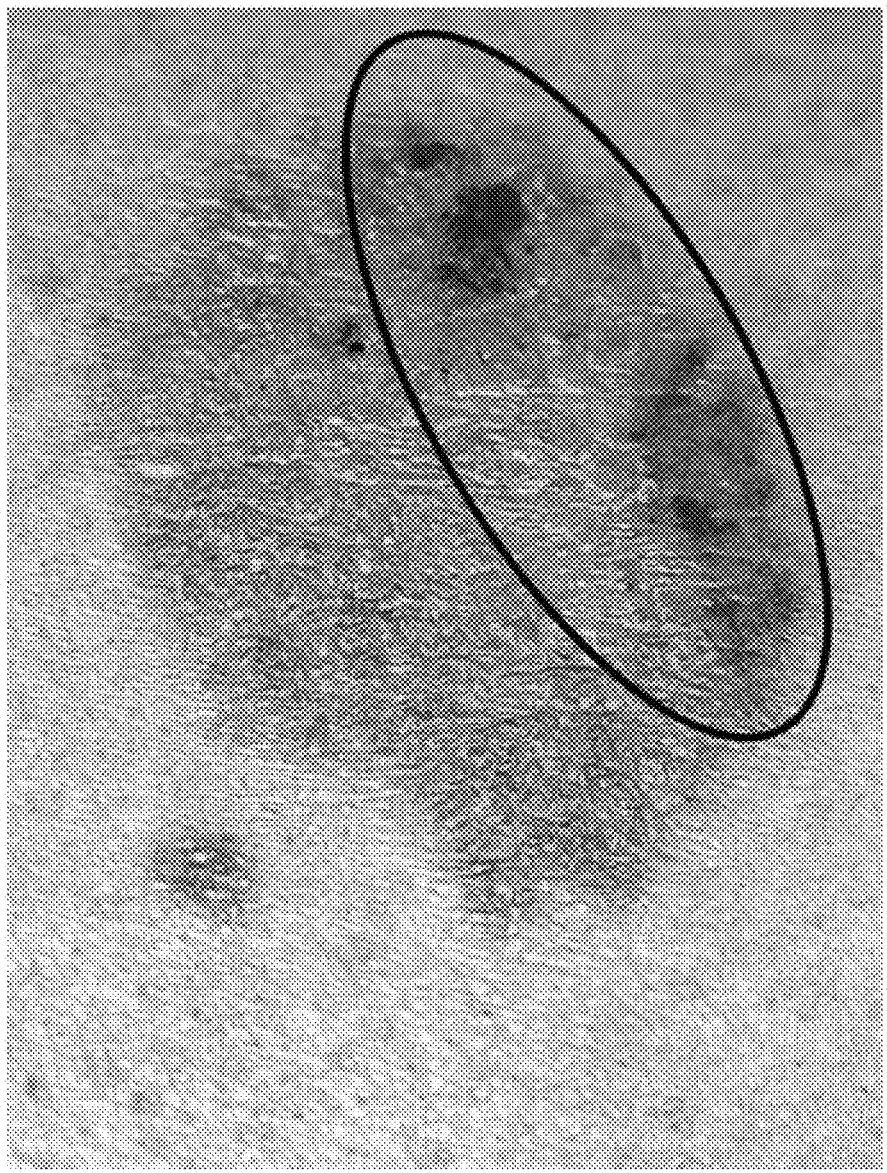
FIG. 8 shows a plaque with the active edge circled on the right shoulder before pre-psoriatic rim treatment.
Figure 9:
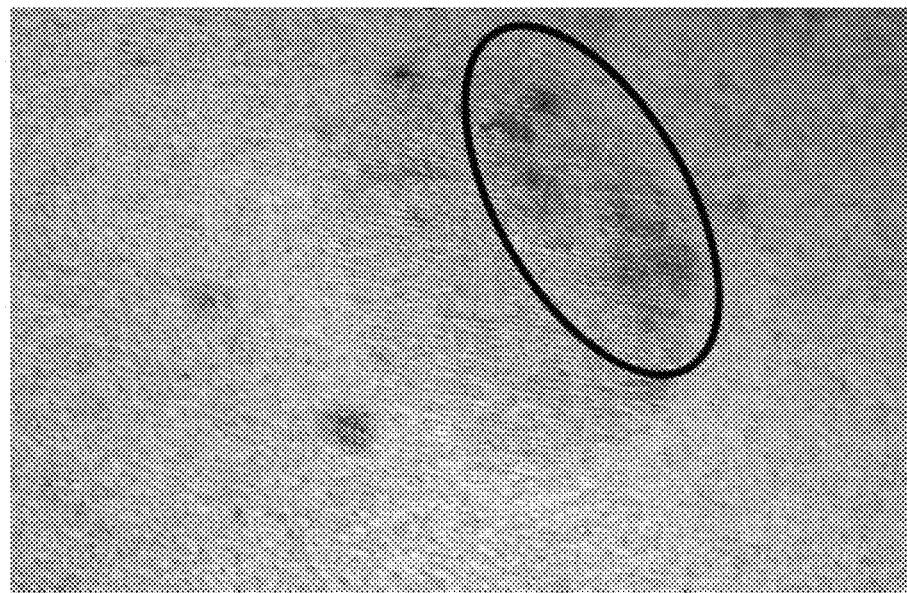
FIG. 9 shows the plaque on the right shoulder with the active edge circled after pre-psoriatic rim treatment.
Figure 10:
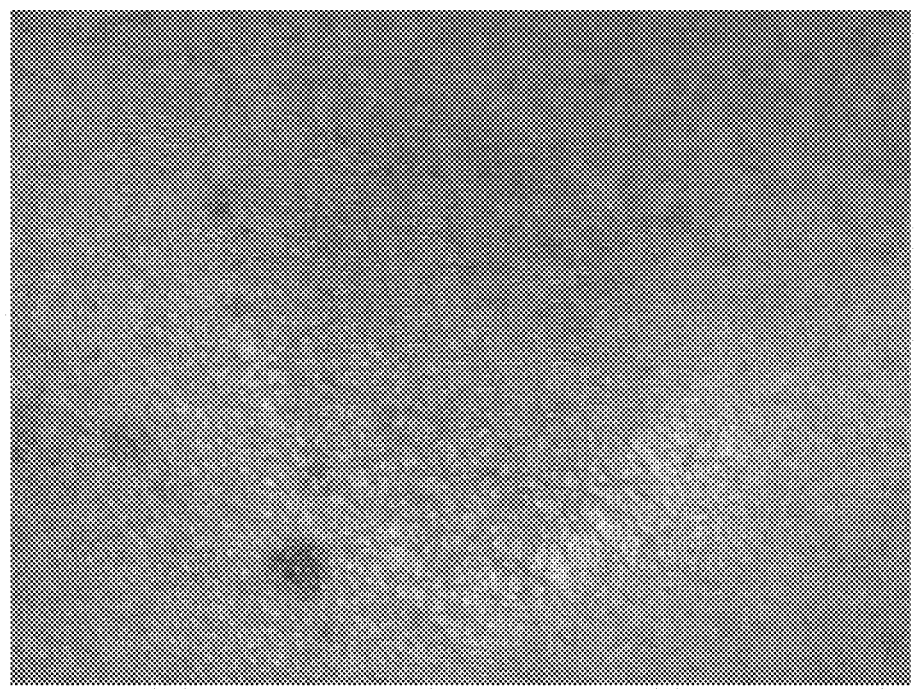
FIG. 10 shows the plaque completely cleared with a faint "colored trace" after pre-psoriatic rim treatment.

The described composition was applied to an area at least partially around the psoriatic lesion(s), termed the pre-psoriatic rim, which was determined using well known laser Doppler flowmetry. As shown in FIGS. 8-10, the results demonstrate the lesion first retreating in the direction of the active edge (FIG. 9) and then clearing completely (FIG. 10). 10 µg/g of the peptide was applied twice daily for 4 weeks. The composition was purposely not applied directly to the lesion.

Without being held to a single theory, a novel local neural transport mechanism appears to be responsible for the effects observed by the pre-psoriatic rim administration resulting in treatment of psoriasis. Topical steroids are usually applied directly on lesions as is the convention for most topical treatments. Topical steroid molecules are much smaller (<500 Da) then CGRP8-37 (3100 Da) and therefore can more easily penetrate thick skin, topical steroids also have a side-effect on normal skin causing skin atrophy in some cases. That is why, for steroids and some other topical remedies e.g. tar (being irritating to normal skin), applying around the lesion is not recommended. Psoriasis lesions have a very thick scaly layer and getting large molecular structures through the skin is problematic. Due to CGRP8-37 molecular size, direct application is thus not likely to be successful for treatment. By applying around the lesion the uncompromised dermal transport layer is used to facilitate the delivery of the CGRP8-37 peptide to the deeper layers of the skin and the site of pathology, resulting in overall greater effectiveness and a possibility for lower dosage and milder side-effects. This low dosage indication has been observed by applying doses as low as 1 µg/g of topical formulation with significant improvement.

As shown in this example, the described composition was administered to an area around a psoriatic lesion to provide treatment of psoriasis. In one embodiment, the approximate area around the lesion required for successful pre-psoriatic rim application is around an inch (~2.5 cm), but is adjusted in proportion to the size of the lesion. This does not require that the composition is only applied around the lesion(s), as depending on the pattern of lesions, some of the topical administration may be applied to the lesion(s) either inadvertently or advertently. This method of pre-psoriatic rim application is most likely to effective on plaque psoriasis, inverse psoriasis and scalp psoriasis. However, the data demonstrate that administration around the lesion(s), i.e., pre-psoriatic rim administration, is required, contrary to typical use of topical treatments for psoriasis, which are directed to be applied directly to the lesion(s). Not shown are numerous unsuccessful applications of CGRP antagonist directly to plaques where the lack of penetration due to the thickness of the skin is the most likely reason for non-response.

EXAMPLE 13

The active edge of a psoriasis lesion has increased blood flow and the macroscopic normal skin shows microscopic early psoriasis changes. This active edge is identified using laser Doppler flowmetry. Earlier immunohistochemical studies on neuropeptides (NPs) in psoriasis skin have shown conflicting results. No defined alterations of specific subsets of peptidergic fibers have been found. The inventors demonstrated, for the first time, that CGRP is increased at the pre-psoriatic rim outside of a psoriasis lesion which later becomes fully psoriatic skin. This information indicates that extralesional, referred to as pre-psoriatic rim, application is the most effective way of treating psoriasis with a CGRP antagonist. The disclosure supports that the source of the increase in CGRP is from outside the lesion, thus treatment should be at this source.

Immunohistochemical studies of neuropeptides (NP) in mature psoriasis skin have shown conflicting results, and no defined changes in neuropeptide have consistently been found (Wallengren et al. Substance p and vasoactive intestinal peptide in bullous and inflammatory skin disease. Acta Derm Venereol, 66(1):23-28, 1986; Pincelli et al. Neuropeptides in skin from patients with atopic dermatitis: an immunohistochemical study. Br J Dermatol, 122(6):745-750, 1990; Anand et al. Neuropeptides in skin disease: increased VIP in eczema and psoriasis but not axillary hyperhidrosis. Br J Dermatol, 124(6):547-549, 1991). Apparently normal skin at the growing edge of the psoriasis lesion has increased blood flow, identified by laser Doppler flow cytometry; histology samples showed early psoriatic changes (Hull et al., active and inactive edges of psoriatic plaques: identification by tracing and investigation by laser-doppler flowmetry and immunocytochemical techniques. J Invest Dermatol, 92(6):782-785, 1989). Investigating this growing area gives more distinguishing results revealing the most active neuropeptide that, when identified, could be important in pathogenesis of psoriasis.

The presence or absence of selected neuropeptides in early psoriasis changes were evaluated and early histological changes that were present were analyzed.

Biopsies were taken from apparently normal skin adjacent to psoriatic lesions, i.e. the pre-psoriatic rim, using non-invasive Laser Doppler Perfusion Imaging (LDPI) technique which was very successful in locating early psoriasis changes. Histological markers were used to evaluate neuropeptides, epidermal keratinocyte proliferation, vascular density, T-cells, neutrophils, and Langerhans cells.

Biopsies using immunohistochemical methods showed increased calcitonin gene-related peptide (CGRP) in eight of eleven biopsies from the pre-psoriatic rim of the psoriasis lesions, compared to the opposite side. Substance P (SP) and vasoactive intestinal peptide (VIP) showed now such changes.

Blood perfusion, keratinocyte proliferation, and T-cell infiltration were increased in very early psoriasis changes where CGRP was also significantly increased. CGRP is a very strong vasodilator, it stimulates keratinocytes growth and is chemotactic for T-cells so may be directly involved in psoriasis pathogenesis and could even be the initiating factor.

Eleven patients with moderate to severe plaque type psoriasis were studied; three women, eight men, ages 26-65 years (Table 1):

| Patient # | Age | Sex | Smoking | Current Treatment | Age at Onset | Genetic | Disease Grade | Biopsy Location |
|---|---|---|---|---|---|---|---|---|
| 1 | 26 | M | − | 0 | 20 | + | Moderate | Back |
| 2 | 41 | M | − | 0 | 23 | ++ | Severe | Left arm |
| 3 | 35 | F | − | 0 | 18 | + | Severe | Left thigh |
| 4 | 35 | F | + | 0 | 17 | ++ | Severe | Left thigh |
| 5 | 54 | F | − | MTX/Remicate | 7 | ++ | Moderate | Right leg |
| 6 | 63 | F | − | 0 | 17 | ++ | Moderate | Right leg |
| 7 | 65 | M | + | 0 | 58 | + | Severe | Back |
| 8 | 48 | M | + | UVB | 34 | + | Moderate | Left leg |
| 9 | 47 | M | + | 0 | 32 | ++ | Moderate | Left leg |
| 10 | 49 | M | − | UVB | 15 | + | Moderate | Left leg |
| 11 | 65 | M | − | 0 | 20 | ++ | Moderate | Right thigh |

Perfusion images (scans) were made of psoriasis plaques and surrounding skin with a PIM II high-resolution laser Doppler perfusion imager and the LDPI Win version 2.1 software (Perimed AB, Järfälla Sweden).

Subject-environmental-technical guidelines for reading of patch tests with the laser were followed (Bjarnason et al. Objective non-invasive assessment of patch tests with the laser doppler perfusion scanning technique. Contact Dermatitis, 40(5):251-260, 1999) except for an 8 cm distance between the aperture of the laser head and tests and low resolution. Those changes were required because of the advancements in high-resolution laser since the guidelines. In addition, a background threshold of 6.2V and a scan size of 64×64 mm measurement sites were made to secure a reasonable skin area surrounding the plaques.

A standard reading speed was used. Perfusion images were analyzed for blood flow and sites were marked for biopsies. Following local anesthesia with lidocaine and adrenaline (20 mg/ml) two 3 mm punch biopsies were taken from each subject; one sample taken from the edge with lower blood perfusion (no. 1 (Inactive)) and another from the edge with higher blood perfusion (no. 2 (Active)).

Figure 11:
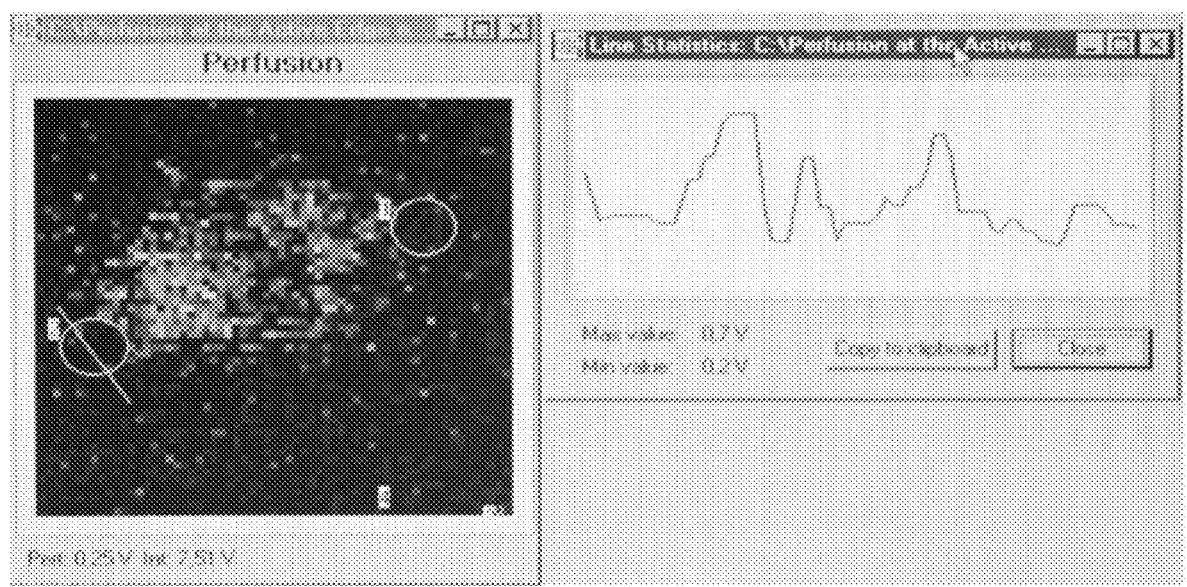
FIG. 11 shows a laser doppler perfusion image of psoriasis plaque and surrounding skin; measurement sites are shown in colors, each which represents a certain perfusion interval; circled areas are from normal skin on the opposite side of the psoriasis lesion (1) and pre-psoriatic rim (2) psoriasis plaque edges; the graph shows perfusion statistics of a line drawn through circle 2.

FIG. 11 shows a typical perfusion scan with the laser. Each measurement site of the scan was assigned a color representing a certain perfusion interval. The psoriasis plaque was located in the middle of the scan where the perfusion was increased. Punch biopsies were taken in the middle of the circled areas. Circle no. 1 is from an inactive edge of the psoriasis plaque with low perfusion while circle no. 2 is from an active edge with high perfusion. A line has been drawn through circle no. 2 on the left side of the figure and the line statistics are shown on the graph. The top of the line in the figure on the left side is on the left of the graph on the right side. The perfusion was higher within the circled area in the middle of the graph compared to the surrounding skin.

Skin samples from eleven individuals with psoriasis were obtained after analysis with Laser Doppler Perfusion Imaging (LDPI). Samples from four individuals were fixed in 10% buffered formaldehyde for 12 hrs and samples from another seven individuals were frozen instantly in liquid nitrogen. The change after four patients attempted to obtain more sensitivity for the immunohistochemical markers. All samples were examined blindly and independently by two pathologists.

Serial sections were cut and mounted on poly-L-lysine-coated glass slides and immunohistochemical studies were done using the following antibodies: factor VIII polyclonal antibody (Ab) (Dako), CD-34 monoclonal Ab (Novocastra), Ki-67 monoclonal Ab (Novocastra); VIP polyclonal Ab monoclonal Ab (BD Biosciences); CD-20 monoclonal Ab (Daco); S-100 polyclonal Ab (Daco).

Frozen (Fr.) and formalin fixed, paraffin-embedded (Par) tissues were sectioned onto silane-coated slides and pre-treated in accord with manufacture's recommendations. Internal positive controls were present on every slide; appropriate negative controls were also performed for each specimen. Primary antibodies were incubated at predetermined dilutions. A biotinylated secondary antibody and streptavidin-peroxidase steps were then performed with the color reaction developed using 3,3-diaminobenzidine as substrate. Sections were counterstained with hematoxylin.

Biopsies were examined for neuropeptides, blood vessels, keratinocyte proliferation neutrophilic infiltration, T-cells, and Langerhans cells. Results from sites 1 and 2 were compared using statistical analysis with Wilcoxon Signed Ranks Test.

Two independent pathologists analyzed the pathological slides blinded for site. Their results were compared statistically using Cohen's Kappa Statistic Test.

The deep dermal and superficial nerve plexus was evaluated specifically for CGRP staining. The staining pattern was overall relatively faint and ranged from an occasional positive nerve fiber (+) to several positive fibers (+++), predominantly in a superficial dermal location.

The dermal deep and superficial nerve plexuses were evaluated specifically for substance P (SP) and vasoactive intestinal peptide (VIP) staining. The staining pattern was negative in most cases or showed an occasional faintly positive nerve fiber (+).

The prominence of the superficial vascular plexus at the papillary-reticular dermal junction was evaluated. Tissue sections were stained with F-VIII and CD-34 respectively to highlight the dermal capillaries. A relatively similar staining pattern was observed with both antibodies. The vascular prominence was scored from + to +++ depending on the number and width of cross-sectioned capillaries in three consecutive papillary dermal regions.

For analysis, a well-oriented field was selected and 150 nuclei were counted. Positive staining was recorded specifically, noting both location and extent. The degree of staining was expressed as numbers of positive cells: + (1-10 cycling cells), ++ (11-20 cycling cells) and +++ (>20 cycling cells).

Dermal papillae capillaries and superficial postcapillary venular plexus were evaluated for the presence or absence of perivascular lymphocytes. The T- and B-cell phenotypes were identified with CD-3 and CD-20 antibodies respectively. The cross-sectioned dermal vessel with the most dense lymphocytic infiltrate was selected and the density of the inflammatory infiltrate was scored as follows: + (1-10 lymphocytes), ++ (10-20 lymphocytes) and +++ (>20 lymphocytes).

The presence of Langerhans cells within the epidermis was evaluated. A well-oriented field was selected and 50 nuclei were counted. The number of positive cells within the field was noted. Histology samples were not available for this analysis from all patients.

The presence or absence of neutrophil exocytosis within the stratum corneum, or stratum spinosum was evaluated as well as neutrophils within the perivascular inflammatory infiltrate.

Figure 15:
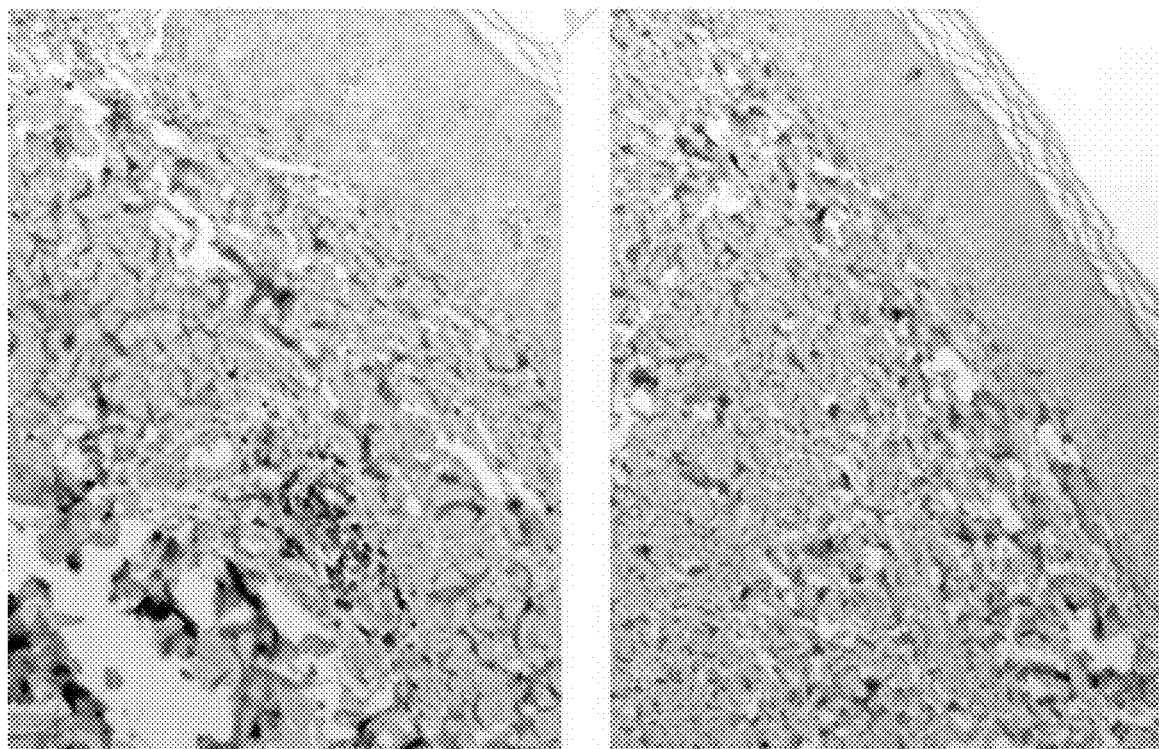
FIG. 15 shows CD-3 in active (left) vs inactive (right) psoriasis.
Figure 17:
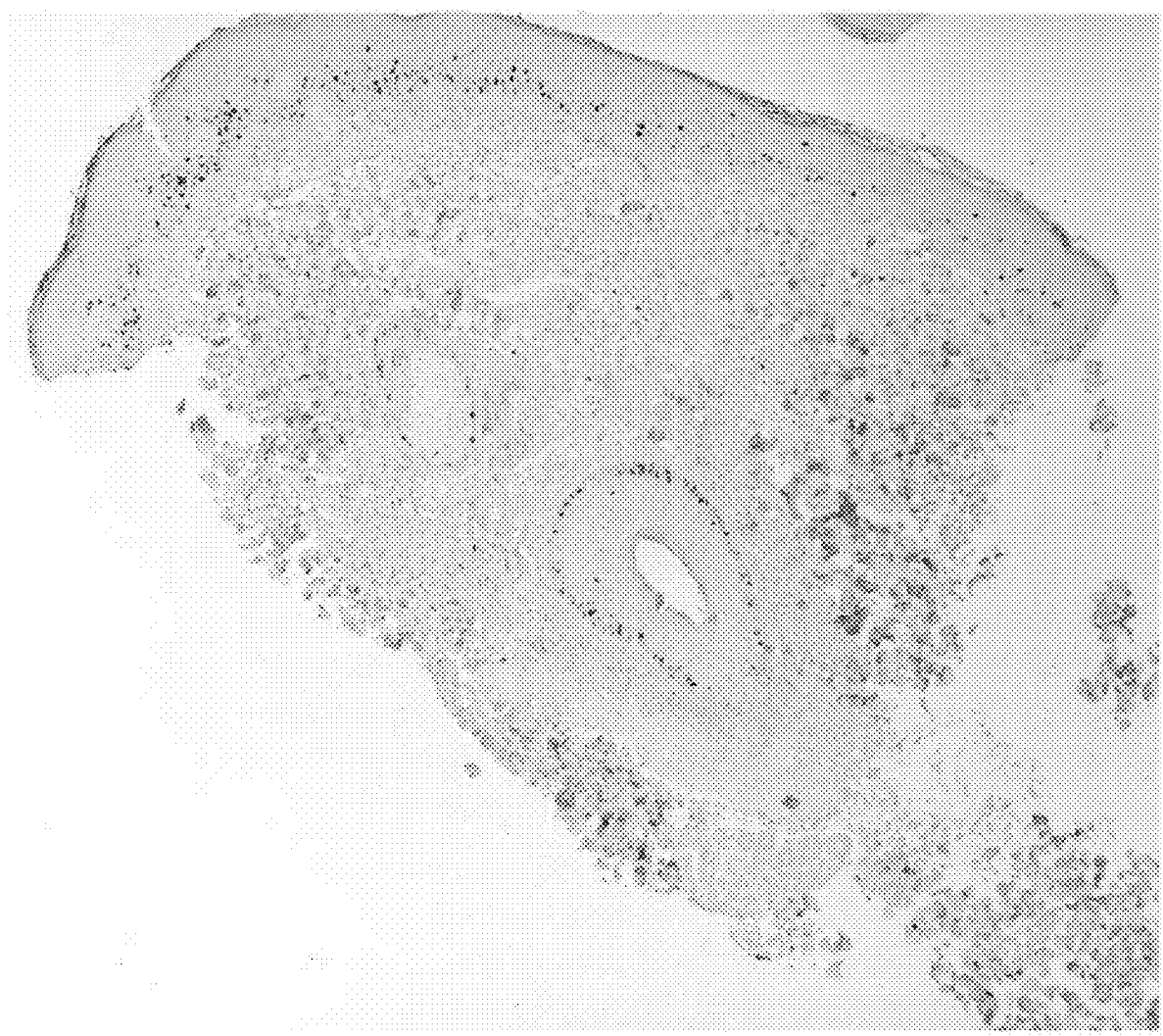
FIG. 17 shows Ki-67 in an active lesion.

Table 2 shows histological comparison between pre-psoriatic skin (biopsy site 2) and normal skin on the opposite side of the psoriasis lesion (biopsy site 1):

(FIG. 17). T-cell infiltration (CD-3) in the dermis was dense in all but two biopsies taken from the active site (FIG. 15). No CD-20 positive cells indicating B-lymphocytes were observed.

Substance P (SP) was detected on staining in 8 of 11 samples. No difference was observed between the two biopsy sites (Table 2). Vasoactive intestinal peptide (VIP) was detected in both biopsies from 2 patients, with equal intensity of staining in both pairs. CGRP was increased in 8 of 11 samples taken from the pre-psoriatic rim compared to

| Patient | Biopsy Site | CGRP | SP | VIP | F-VIII | Ki = 67 | T | N | APC |
|---|---|---|---|---|---|---|---|---|---|
| 1(Par) | 1 | + | 0 | 0 | + | + | 0 | 0 | 9 |
|  | 2 | + | 0 | 0 | ++ | ++ | ++ | 0 | 6 |
| 2(Par) | 1 | 0 | + | 0 | + | + | + | 0 | 8 |
|  | 2 | +++ | + | 0 | +++ | +++ | + | 0 | 3 |
| 3(Par) | 1 | 0 | 0 | 0 | + | + | + | 0 | 11 |
|  | 2 | 0 | 0 | 0 | +++ | +++ | ++ | 0 | 7 |
| 4(Par) | 1 | 0 | + | + | + | + | + | 0 | 8 |
|  | 2 | +++ | + | + | +++ | ++ | +++ | 0 | 3 |
| 5(Fr.) | 1 | + | + | 0 | + | + | + | 0 | 7 |
|  | 2 | +++ | + | 0 | +++ | +++ | +++ | 0 | 4 |
| 6(Fr.) | 1 | + | 0 | 0 | + | + | + | 0 | 9 |
|  | 2 | + | 0 | 0 | ++ | +++ | +++ | 0 | 4 |
| 7(Fr.) | 1 | 0 | + | 0 | + | + | + | 0 | n/a |
|  | 2 | +++ | + | 0 | ++ | +++ | +++ | 0 |  |
| 8(Fr.) | 1 | + | + | + | + | + | + | 0 | 6 |
|  | 2 | ++ | + | + | +++ | ++ | + | 0 | 5 |
| 9(Fr.) | 1 | 0 | + | 0 | + | + | + | 0 | 9 |
|  | 2 | ++ | + | 0 | ++ | +++ | ++ | 0 | 6 |
| 10(Fr.) | 1 | 0 | + | 0 | + | + | + | 0 | n/a |
|  | 2 | +++ | + | 0 | +++ | +++ | ++ | 0 |  |
| 11(Fr.) | 1 | 0 | + | 0 | + | + | + | 0 | n/a |
|  | 2 | ++ | + | 0 | +++ | ++ | +++ | 0 |  |
| P value |  | 0.001 | nss | nss | 0.003 | 0.003 |  |  |  |
| Psoriasis |  | +++ | + | + | +++ | +++ | +++ | +++ | 2 |
| Control |  | 0 | 0− | 0 | + | + | + | 0 | 10 |

Use of laser Doppler permitted identification of areas outside psoriasis lesions where histopathology changes of early psoriasis lesions could be detected. Two opposite sides (poles) of the psoriasis lesions could be detected with quite different histology.

Figure 12:
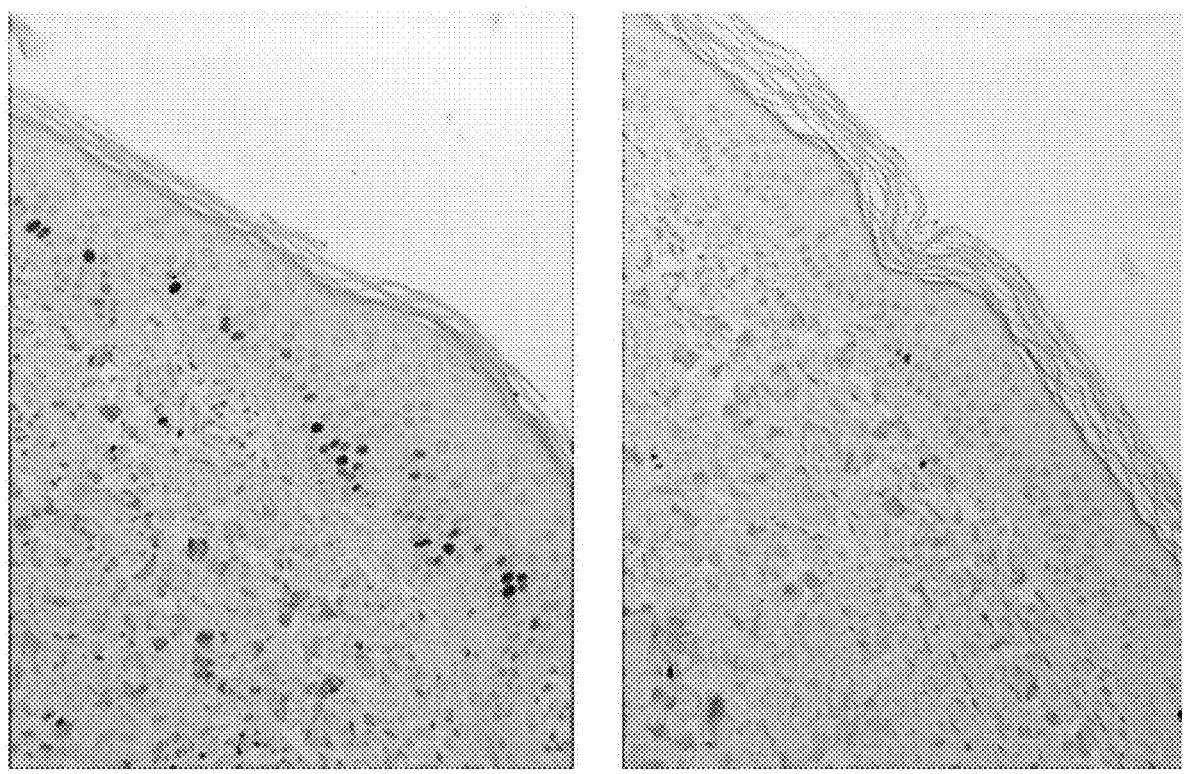
FIG. 12 shows Ki-67 in active (left) vs inactive (right) psoriasis.

Biopsies from macroscopic normal looking skin showed either psoriasis in its earliest phase or almost normal morphology. These two areas were compared in regard to various histochemical and immunohistochemical markers. The active site had increased keratinocyte proliferation (Ki 67) in the basal layer compared to the inactive site (p=0.003, FIG. 12).

Figure 13:
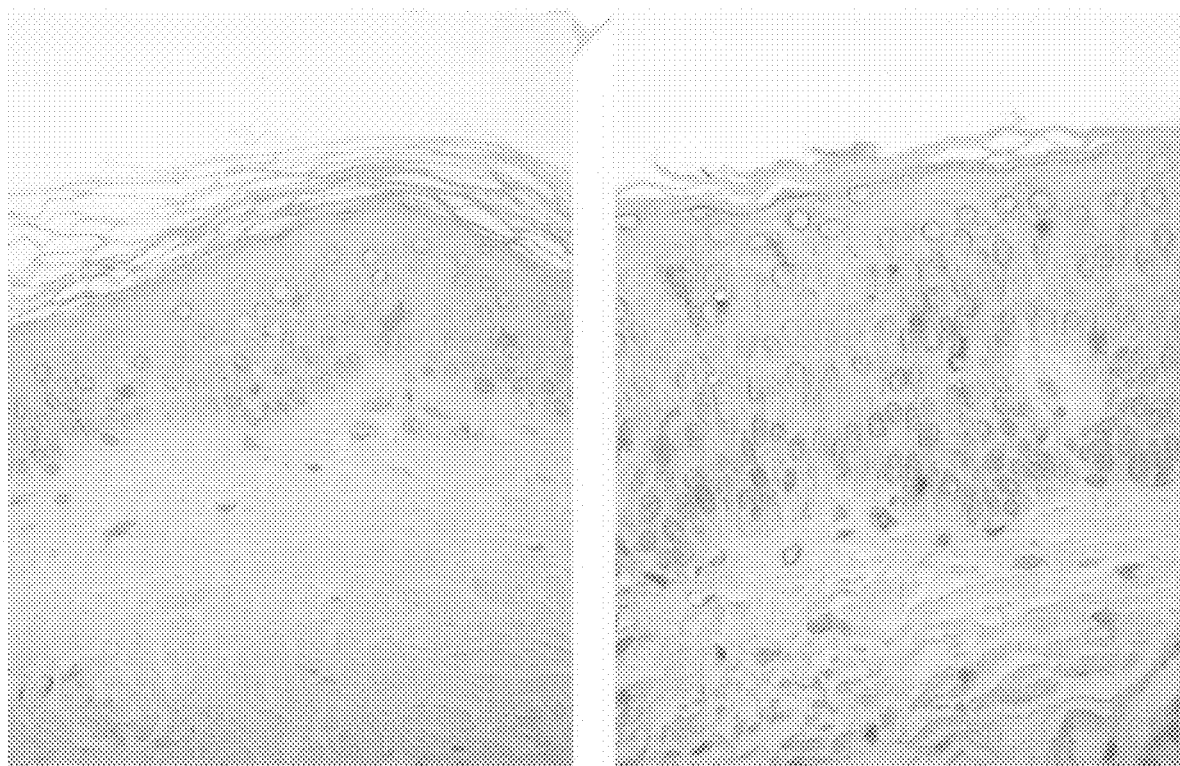
FIG. 13 shows Langerhans Cells (LC) in active (left) vs inactive (right) psoriasis.
Figure 14:
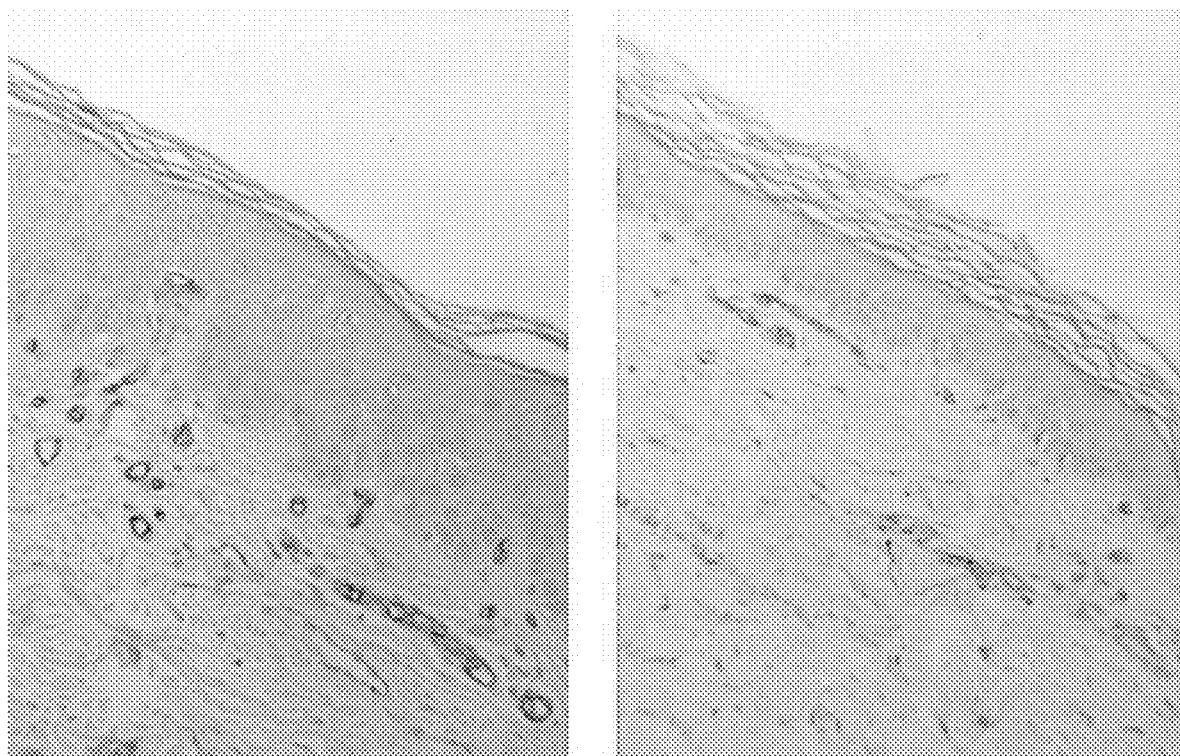
FIG. 14 shows F-VIII in active (left) vs inactive (right) psoriasis.

Epidermis in the active site showed no signs of acanthosis, parakeratosis, or disruption of the basket wave structure of the stratum corneum (hemotoxylin-eosin stained slides). Keratinocyte morphology was normal and the granular layer which often is absent in psoriasis was still intact. There were no infiltration of neutrophils in the epidermis or dermis. Langerhans cells (LC) were fewer than in the inactive site shown by S-100 staining in the active site, and their dendrites appeared short and sometimes absent (FIG. 13). In the dermis, dilated vessels were prominent in early lesions demonstrated clearly by staining for vonWillebrand factor (p=0.003, FIG. 14).

Figure 16:
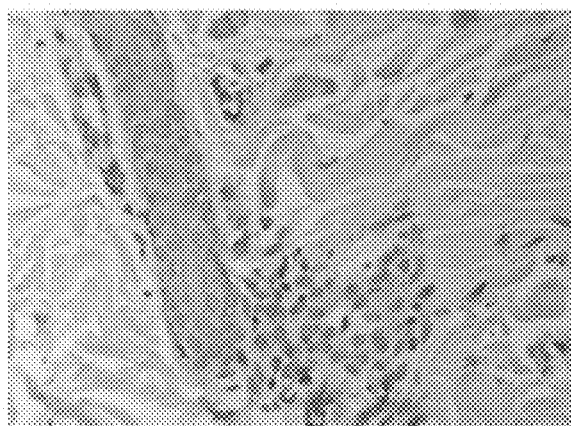
FIG. 16 shows CGRP 3 in active (left) vs inactive (right) psoriasis.
Figure 16:
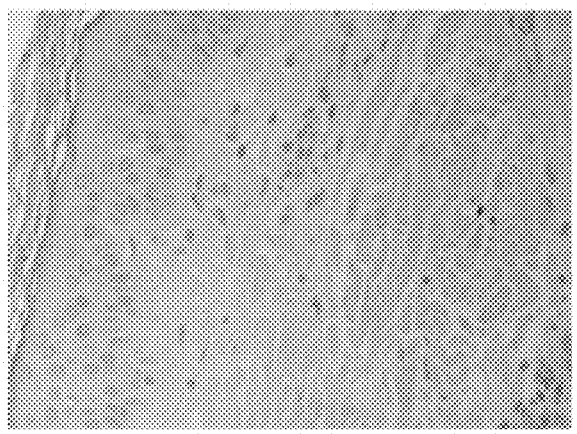

Vascular pattern and keratinocyte proliferation differences between the two sides (poles) were seen in all sample pairs (Table 2). Proliferating keratinocytes on the active site were seen on some slides in the outer routh (the outermost layer of the hair follicle which is known to contain epidermic stem cells) sheet of follicles, indicating involvement of stem cells the normal skin on the opposite side of the psoriasis lesion (p=0.001, FIG. 16). CGRP was often detected around hair follicles (FIG. 16) and was detected in low intensity in 4 of 11 samples on the inactive site.

The data demonstrate novel very early changes in psoriasis, with special reference to the neuropeptide CGRP. Skin samples evaluated were taken from clinically normal looking skin, showing no acanthosis nor changes in the stratum corneum. CGRP was increased in these early psoriasis samples simultaneously with the hallmarks of psoriasis i.e. vasodilation, keratinocyte proliferation, and T-cell infiltration. CGRP can initiate all these changes beside being a strong suppressor of Langerhans cells (APC), indicating CGRP plays a major role in psoriasis.

CGRP was a specific stimulator of T-cell migration into 3D collagen type I matrices, whereas a number of other neuropeptides and opioids did not influence T cell infiltration. CGRP significantly stimulated migration of non-activated and anti-CD3 activated T-lymphocytes. Virtually all migrating cells were CD3+ (>96%) and CGRP did not stimulate B-cell migration (Talme et al., The neuropeptide calcitonin gene-related peptide (CGRP) stimulates t cell migration into collagen matrices. J Neuroimmunol, 196(1-2):60-6, May 2008). The same lymphocyte profile was seen, indicating a nonspecific T-cell immune response (innate immunity).

Langerhans cells antigen presenting cells (APC) are the central cells in many models of the T-cell theory even though some studies have shown them to be reduced in psoriasis. Marked decrease in density of Langerhans cell population in psoriatic plaques was shown using ATPase histochemical staining of frozen skin sections (Kierland, Psoriasis: Proceedings of the international symposium-Stanford University 1971). There was marked decrease in the density of the Langerhans cell population in psoriatic plaques, restored after successful treatment with methotrexate and Goeckerman Regimen (Archives of Dermatology, 106 (1972) 137). The inventors demonstrated that Langerhans cells were not only decreased but also showed signs of suppression, seen by marked reduction of dendrites. This is the first time these changes were seen as a part of very early psoriasis changes present alongside keratinocyte proliferation and immune cell infiltration.

Immunohistochemical staining in early psoriasis revealed CGRP confined to nerve endings. CGRP might also originate from other sources. Human lymphocytes can produce CGRP (Wang et al., Production and secretion of calcitonin gene-related peptide from human lymphocytes. J Neuroimmunol, 130(1-2):155-162, 2002; Nickoloff and Nestle. Recent insights into the immunopathogenesis of psoriasis provide new therapeutic opportunities. J Clin Invest, 113 (12):1664-1675, 2004). T-cells activated by IL-2 produce high amount of CGRP (Xing et al., Induction and expression of beta-calcitonin gene-related peptide in rat t lymphocytes and its significance. J Immunol, 165(8):4359-4366, 2000). Increased CGRP activity or secretion need not be limited to injured or altered nerve function, it could be secondary to altered immune response involving T-cells, or could be a second step in the events of inflammation or the wound healing process for T-cells to continue CGRP production. In the SCID mouse model system, IL-2 is used to activate T-cells before they are injected into skin grafts. These activated T-cells stimulate a psoriasis phenotype in the grafts (Wrone-Smith and Nickoloff, Dermal injection of immunocytes induces psoriasis. J Clin Invest, 98(8):1878-1887, 1996; Nickoloff et al. Characterization of a t cell line bearing natural killer receptors and capable of creating psoriasis in a SCID mouse model system. J Dermatol Sci, 24(3):212-225, 2000).

Activated T-cells may in fact produce increased amounts of CGRP. Theories of T-cell activation and nerve dysfunction can be combined through increased CGRP activity. Many possible dysfunctions can lead to this increased activity. Psoriasis is likely not one disease but several diseases sharing a final common pathway. These data are the first to demonstrate increased CGRP in early psoriasis lesions that may be the sole cause of the pathophysiology seen in psoriasis.

The embodiments shown and described in the specification are only specific embodiments of the inventor who is skilled in the art and are not limiting in any way. Therefore, various changes, modifications, or alterations to those embodiments may be made without departing from the spirit of the invention in the scope of the following claims. References cited are expressly incorporated by reference herein in their entirety.

What is claimed is:

1. A method of treating psoriasis in an individual in need thereof, the method comprising topically administering to a pre-psoriatic rim of the individual a pharmaceutical composition comprising a therapeutically effective dose of a calcitonin gene-related peptide (CGRP) antagonist, wherein the CGRP antagonist is heparin, and wherein the pre-psoriatic rim is a normal looking skin that is substantially adjacent to a psoriatic lesion and characterized by at least one of the following as compared to normal skin: increased CGRP activity, increased blood flow, fewer Langerhans cells, increased dilation of blood vessels, and increased T-cell infiltration.

2. The method of claim 1, wherein the pharmaceutical composition is applied at least twice daily at the pre-psoriatic rim.

* * * * *

SEQUENCE LISTING

```
<160> NUMBER OF SEQ ID NOS: 2

<210> SEQ ID NO 1
<211> LENGTH: 30
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 1

Val Thr His Arg Leu Ala Gly Leu Leu Ser Arg Ser Gly Gly Met Val
1               5                   10                  15

Lys Ser Asn Phe Val Pro Thr Asn Val Gly Ser Lys Ala Phe
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 2

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30
```